United States Patent
Clark et al.

(10) Patent No.: US 6,172,062 B1
(45) Date of Patent: *Jan. 9, 2001

(54) DIHYDROBENZODIOXINE CARBOXAMIDE AND KETONE DERIVATIVES

(75) Inventors: Robin Douglas Clark, Palo Alto; Alam Jahangir, San Jose, both of CA (US)

(73) Assignee: Syntex (USA) LLC, Palo Alto, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/392,195

(22) Filed: Sep. 2, 1999

Related U.S. Application Data

(60) Provisional application No. 60/138,468, filed on Jun. 10, 1999, and provisional application No. 60/099,740, filed on Sep. 10, 1998.

(51) Int. Cl.[7] .................. A61K 31/5377; A61N 13/00; C07D 403/12; C07D 413/14
(52) U.S. Cl. .................. 514/233.8; 514/253; 544/130; 544/364; 546/16; 546/187
(58) Field of Search .................. 544/130, 364; 546/187; 514/233.8

(56) References Cited

U.S. PATENT DOCUMENTS

| | | |
|---|---|---|
| 5,185,335 | 2/1993 | Van Daele et al. . |
| 5,262,418 | 11/1993 | Van Daele et al. . |
| 5,374,637 | 12/1994 | Van Daele et al. . |
| 5,472,866 | 12/1995 | Gerald et al. . |
| 5,521,314 | 5/1996 | Van Daele et al. . |
| 5,536,733 | 7/1996 | Van Daele et al. . |
| 5,552,553 | 9/1996 | Van Daele et al. . |
| 5,554,722 | 9/1996 | Van Daele et al. . |
| 5,565,582 | 10/1996 | Van Daele et al. . |
| 5,576,448 | 11/1996 | Van Daele et al. . |

(List continued on next page.)

FOREIGN PATENT DOCUMENTS

| | | |
|---|---|---|
| 0445 862 A2 | 9/1991 | (EP) . |
| WO 93/18036 * | 9/1993 | (EP) . |
| 0 389 037 B1 * | 9/1995 | (EP) . |
| 0 700 383 B1 * | 9/1998 | (EP) . |
| 924 1241 * | 3/1996 | (JP) . |
| 11001472 * | 1/1999 | (JP) . |
| WO 93/03725 * | 3/1993 | (WO) . |
| WO 93/05038 * | 3/1993 | (WO) . |
| WO 93/16072 * | 8/1993 | (WO) . |
| WO 94/05654 * | 3/1994 | (WO) . |
| WO 94/08994 * | 4/1994 | (WO) . |
| WO 94/08995 * | 4/1994 | (WO) . |
| WO 94/10174 * | 5/1994 | (WO) . |
| WO 94/17071 * | 8/1994 | (WO) . |

(List continued on next page.)

OTHER PUBLICATIONS

Sarges et al, *Chemical Abstracts*, vol. 84, No. 144,565, 1976.
Clark R.D. et al., "5–HT4 Receptors in the Brain and Periphery," Springer–Verlag Berlin and R.G. Landes Company Georgetown, TX, pp 1–48, 1998.
Clark, R.D. et al ., "Bioorganic & Medicinal Chem. Letters," 2119–2122, 1995.
Clark, R.D. et al., Bioorganic & Medicinal Chem. Letters, 4(20) 2477–2480 1994.
Waikar M.V. et al., "Evidence for an inhibitory 5–HT4 Receptor in Urinary Bladder of Rhesus and Cynomolgus Monkeys," Br. J. Pharmacol. Pp 213–218, 1994.

(List continued on next page.)

Primary Examiner—Robert Ramsuer
(74) Attorney, Agent, or Firm—Janet Kaku; Janet Pauline Clark

(57) ABSTRACT

This invention relates to certain 5-HT$_4$ receptor modulators, particularly 5-HT$_4$ receptor antagonists, represented by Formula I:

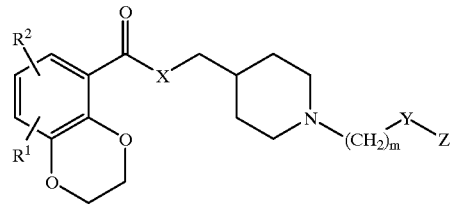

I wherein Z is formula (A) or (B):

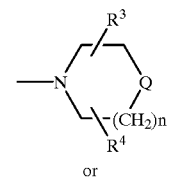

(A)

or

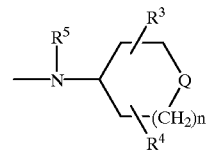

(B)

wherein $R^1$, $R^2$, $R^3$, $R^4$, and $R^5$ and the other substituents are as defined in the specification; or individual isomers, racemic or non-racemic mixtures of isomers, and pharmaceutically acceptable salts or solvates thereof. The invention further relates to pharmaceutical compositions containing such compounds and methods for their use as therapeutic agents.

38 Claims, No Drawings

U.S. PATENT DOCUMENTS

| | | |
|---|---|---|
| 5,580,885 | 12/1996 | King et al. . |
| 5,602,129 | 2/1997 | Van Daele et al. . |
| 5,610,157 | 3/1997 | Van Daele et al. . |
| 5,616,583 | 4/1997 | Van Daele et al. . |
| 5,616,738 | 4/1997 | Van Daele et al. . |
| 5,620,992 | 4/1997 | King et al. . |
| 5,654,320 | 8/1997 | Catlow et al. . |
| 5,705,498 | 1/1998 | Gaster et al. . |
| 5,705,509 | 1/1998 | Gaster et al. . |
| 5,708,174 | 1/1998 | King et al. . |
| 5,739,134 | 4/1998 | Van Daele et al. . |
| 5,741,801 | 4/1998 | King et al. . |
| 5,763,458 | 6/1998 | Clark et al. . |
| 5,766,879 | 6/1998 | Gerald et al. . |
| 5,786,372 | 7/1998 | King et al. . |
| 5,798,367 | 8/1998 | Catlow et al. . |
| 5,852,014 | 12/1998 | Gaster et al. . |
| 5,872,134 | 2/1999 | King et al. . |
| 5,998,409 | 12/1999 | Gaster et al. . |
| 6,069,152 | 5/2000 | Schaus et al. . |

FOREIGN PATENT DOCUMENTS

| | | | |
|---|---|---|---|
| WO 96/05166 | * | 8/1994 | (WO) . |
| WO 94/27987 | * | 10/1994 | (WO) . |
| WO 94/29298 | * | 12/1994 | (WO) . |
| WO 94/27965 A1 | | 12/1994 | (WO) . |
| WO 98/27058 | * | 6/1998 | (WO) . |
| WO 99/28456 | * | 6/1999 | (WO) . |

OTHER PUBLICATIONS

Hedge, "5–HT4 Receptors in Gastrointestinal Tract," Landes Company Austin, TX pp 150–169, 1997.

Anthony Ford et al., "5–HT4 Receptors in Lower Tract Tissues," Landes Company Austin, TX pp 173–193, 1997.

* cited by examiner

DIHYDROBENZODIOXINE CARBOXAMIDE AND KETONE DERIVATIVES

CROSS-REFERENCE TO RELATED APPLICATIONS

This U.S. Patent Application claims priority under 35 U.S.C.119(e) to U.S. Provisional Application Ser. No. 60/138,468, filed Jun. 10, 1999, incorporated herein by reference in its entirety, and U.S. Provisional Application Ser. No. 60/099,740, filed Sep. 10, 1998, incorporated herein by reference in its entirety.

BACKGROUND OF THE INVENTION

1. Field of the Invention

This invention relates to $5\text{-}HT_4$ receptor modulators, particularly $5\text{-}HT_4$ receptor antagonists, especially certain dihydrobenzodioxine carboxamide and ketone derivatives, and associated pharmaceutical compositions containing them and methods for their use as therapeutic agents.

2. Background of the Invention

Serotonin, a neurotransmitter with mixed and complex pharmacological characteristics, was first discovered in 1948 and has since been the subject of substantial research. Serotonin, also referred to as 5-hydroxy-tryptamine (5-HT), acts both centrally and peripherally on discrete 5-HT receptors. The 5-HT receptor family is presently delineated into seven major subclassifications, $5\text{-}HT_1$, $5\text{-}HT_2$, $5\text{-}HT_3$, $5\text{-}HT_4$, $5\text{-}HT_5$, $5\text{-}HT_6$, and $5\text{-}HT_7$, each of which may a heterogeneous.

The $5\text{-}HT_4$ receptors are widely distributed throughout the body and have various functions. For example, the $5\text{-}HT_4$ receptors located on postganglionic parasympathetic autonomic efferent neurons of the urinary bladder mediate facilitation of neurogenic bladder detrusor contractions (see Ford, A. P. D. W. and Kava, M. S., 5-HT4 *Receptors in the Brain and Periphery*, Eglen, R. M., Ed., Springer-Verlag Berlin and R.G. Landes Company Georgetown, Tex., 1998, pp 171–193; Waikar, M. V. etal., *Br. J. Pharmacol.* 1994, 111, 213–218; Corsi, M. et al., *Br. J. Pharmacol.* 1991, 104, 719–725). In the central nervous system, the $5\text{-}HT_4$ receptors are found on neurons of the superior and inferior colliculi and in the hippocampus, and are thought to be involved in areas of the central nervous system affecting anxiety, depression, cognition, substance dependency, schizophrenia, appetite, thermoregulation, and such. In the gastrointestinal tract, the $5\text{-}HT_4$ receptors are found on neurons, e.g., myenteric plexus, as well as on smooth muscle and secretory cells, and appear to modulate gastrointestinal motility, evoke secretion in the alimentary tract, and stimulate cholenergic excitatory pathways involved in the peristaltic reflex (see Hegde, S. S., 5-HT4 *Receptors in the Brain and Periphery*; Eglen, R. M., Ed., Springer-Verlag Berlin and R.G. Landes Company Georgetown, Tex., 1998, pp 150–169). In the cardiovascular system, the $5\text{-}HT_4$ receptors mediate 5-HT induced positive inotrophy and chronotropy in atrial myocytes, e.g., bradyarrhythmia or tachyarrhythmia (see Kaumann, A. et al., *Naunyn-Schmiedeberg's Arch. Pharmacol.*, 1991, 344, 150–159).

Thus, it is clear that $5\text{-}HT_4$ receptor antagonists will offer distinct therapeutic advantages collectively in efficacy and rapidity of onset, particularly in urinary tract disorders related to autonomic mediation of storage and voiding reflexes. Additionally, because the $5\text{-}HT_4$ receptors found in other organs, e.g., the heart or gastrointestinal tract, are not essential for basic physiological function, minimal side effects are anticipated with improved tolerability (see Ford, A. P. D. W. and Kava, M. S., supra). The compounds of the present invention provide such advantages.

3. Description of the Related Art

U.S. Pat. No. 5,852,014 and PCT Published Application WO 93/18036 (Gaster et al.) refer to certain condensed indole carboxamide derivatives which are disclosed as having $5\text{-}HT_4$ receptor antagonist activity useful for treating gastrointestinal, cardiovascular, and CNS disorders.

U.S. Pat. No. 5,763,458 (Clark et al.) and European Patent EP 0 700 383 B1 refer to certain dihydrobenzodioxine-propan-1-one derivatives which are disclosed as $5\text{-}HT_4$ ligands.

U.S. Pat. Nos. 5,741,801 and 5,872,134, and PCT Published Application WO 94/27987 (King et al.) refer to certain dihydrobenzodioxine-propan-1-one derivatives which are disclosed as having $5\text{-}HT_4$ receptor antagonist activity useful for treating gastrointestinal, cardiovascular or CNS disorders.

U.S. Pat. No. 5,708,174 and PCT Published Application WO 94/08994 (King et al.) refer to certain heterocyclic carboxylate derivatives which are disclosed as having $5\text{-}HT_4$ receptor antagonist activity useful for treating gastrointestinal, cardiovascular, and CNS disorders.

U.S. Pat. No. 5,705,509 and PCT Published Application WO 94/17071 (Gaster et al.) refer to certain heterocyclic carboxylate derivatives which are disclosed as having $5\text{-}HT_4$ receptor antagonist activity useful for treating gastrointestinal, cardiovascular, and CNS disorders.

U.S. Pat. No. 5,705,498 and PCT Published Application WO 94/10174 (Gaster et al.) refer to certain dihydrobenzodioxine carboxamide derivatives which are disclosed as being useful in manufacturing medicaments for $5\text{-}HT_4$ receptor antagonists.

U.S. Pat. Nos. 5,654,320 and 5,798,367 (Catlow et al.) refer to certain indazole carboxamide derivatives which are disclosed as having $5\text{-}HT_4$ receptor partial agonist and antagonist activity.

U.S. Pat. Nos. 5,620,992 and 5,786,372, and PCT Published Application WO 94/05654 (King et al.) refer to certain dihydrobenzodioxine carboxylate derivatives which are disclosed as having $5\text{-}HT_4$ receptor antagonist activity.

U.S. Pat. No. 5,580,885 and PCT Published Application WO 93/05038 (King et al.) refer to certain dihydrobenzodioxine carboxamide derivatives which are disclosed as having $5\text{-}HT_4$ receptor antagonist activity.

U.S. Pat. Nos. 5,374,637, 5,521,314, 5,536,733, 5,552, 553, 5,554,772, 5,565,582, 5,576,448, 5,602,129, 5,610,157, 5,616,583, 5,616,738, and 5,739,134, and European Patent EP 0 389 037 B1, (Van Daele et al.) refer to certain dihydrobenzodioxine carboxamide derivatives which are disclosed as having gastrointestinal motility stimulating properties.

U.S. Pat. Nos. 5,185,335 and 5,262,418 (Van Daele et al.) refer to certain dihydrobenzodioxine carboxamide derivatives which are disclosed as having gastrointestinal motility stimulating properties.

PCT Published Application WO 98/27058 (Bromidge et al.) refers to certain benzamide derivatives which are disclosed as having $5\text{-}HT_6$ receptor activity.

PCT Published Application. WO 96/05166 (assigned to Yamanouchi) refers to certain heterocyclic-substituted alkyl-heterocycloalkylamine derivatives which are disclosed as having $5\text{-}HT_4$ receptor agonist activity useful for treating CNS disorders and digestive tract movement.

PCT Published Application WO 94/29298 (Gaster et al.) refer to certain dihydrobenzodioxine carboxylate derivatives which are disclosed as having 5-HT$_4$ receptor antagonist activity useful for treating gastrointestinal, cardiovascular, and CNS disorders.

PCT Published Application WO 94/08995 (Gaster et al.) refers to certain heterocyclic carboxamide derivatives which are disclosed as having 5-HT$_4$ receptor antagonist activity useful for treating gastrointestinal, cardiovascular, and CNS disorders.

PCT Published Application WO 93/16072 (King et al.) refers to certain heterocyclic carboxamide derivatives which are disclosed as having 5-HT$_4$ receptor antagonist activity useful for treating gastrointestinal, cardiovascular, and CNS disorders.

PCT Published Application WO 93/03725 (King et al.) refers to certain heterocyclic carboxamide derivatives which are disclosed as having 5-HT$_4$ receptor antagonist activity.

Japanese Patent Application JP 11001472 (assigned to Dainippon Pharm) refers to certain benzamide derivatives which are disclosed as having 5-HT$_4$ receptor antagonist activity useful for the prevention and treatment of digestive disorders.

Japanese Patent Application JP 9241241 (assigned to Morishita Roussel) refers to certain N-(1-substituted-4-piperidyl)benzamide derivatives which are disclosed as being selective 5-HT$_4$ receptor inhibitors useful for treating chronic gastritis, CNS disorders and urological diseases.

Clark, R. D., *5-HT4 Receptors in the Brain and Periphery*; Eglen, R. M., Ed., Springer-Verlag Berlin and R.G. Landes Company Georgetown, Tex., 1998, pp 1–48, refers to the medicinal chemistry of certain 5-HT$_4$ receptor ligands.

Clark, R. D. et al., *Bioorganic & Medicinal Chem. Letters*. 1995, 5(18), 2119–2122, refers to certain benzodioxanyl ketone derivatives having 5-HT$_4$ receptor antagonist activity.

Clark, R. D. et al., *Bioorganic & Medicinal Chem. Letters*. 1994, 4(20) 2477–2480, refers to certain benzoate derivatives having 5-HT$_4$ partial agonist activity.

All publications, patents, and patent applications cited herein, whether supra or infra, are each hereby incorporated by reference in their entirety.

SUMMARY OF THE INVENTION

This invention relates to compounds comprising Formula I:

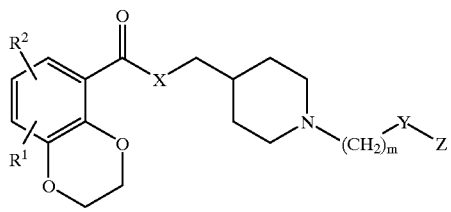

wherein:
$R^1$ and $R^2$ are each independently in each occurrence hydrogen, lower alkyl, alkoxy, halogen, amino, or hydroxy;
X is independently in each occurrence —NH or —CH$_2$;
m is independently in each occurrence an integer 2, 3, or 4;
Y is independently in each occurrence —SO$_2$;
Z is independently in each occurrence formula (A) or (B):

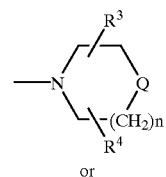

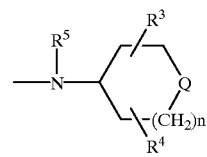

wherein:
$R^3$, $R^4$, and $R^5$ are each independently in each occurrence hydrogen or lower alkyl;
Q is independently in each occurrence O, S, —NR$^6$, or —CR$^7$R$^8$;
n is independently in each occurrence an integer 1 or 2;
wherein:
$R^6$ is independently in each occurrence hydrogen, lower alkyl, cycloalkyl, heterocyclyl, heteroaryl, —COR$^9$, —SO$_2$R$^9$, —CON R$^{10}$R$^{11}$, —SO$_2$NR$^{10}$R$^{11}$, or aryl optionally mono- or di-substituted with halogen or lower alkyl;
$R^7$ is independently in each occurrence hydrogen or lower alkyl;
$R^8$ is independently in each occurrence hydrogen, lower alkyl, alkoxy, aryloxy, —(CH$_2$)$_p$CONR$^{10}$R$^{11}$, —(CH$_2$)$_p$SO$_2$NR$^{10}$R$^{11}$, —(CH$_2$)$_p$NR$^7$COR$^9$, or —(CH$_2$)$_p$NR$^7$SO$_2$R$^9$; or
$R^7$ and $R^8$ taken together with the common ring carbon to which they are attached form a monocyclic saturated 5- or 6-membered ring optionally independently containing 0 or 1 heteroatom of nitrogen, oxygen, or sulfur;
wherein:
$R^9$ is independently in each occurrence lower alkyl, heteroaryl, heterocyclyl, or aryl optionally mono- or di-substituted with halogen or lower alkyl;
$R^{10}$ and $R^{11}$ are each independently hydrogen or lower alkyl; and
p is independently in each occurrence an integer 0, 1, 2, 3, or 4;

or individual isomers, racemic or non-racemic mixtures of isomers, or pharmaceutically acceptable salts or solvates thereof.

This invention further relates to pharmaceutical compositions comprising a therapeutically effective amount of at least one compound of Formula I, or individual isomers, racemic or non-racemic mixtures of isomers, or pharmaceutically acceptable salts or solvates thereof, in admixture with at least one suitable carrier. In a preferred embodiment, the pharmaceutical compositions are suitable for administration to a subject having a disease state that is alleviated by treatment with a 5-HT$_4$ receptor modulator, particularly a 5-HT$_4$ receptor antagonist.

This invention further relates to pharmaceutical compositions suitable for administration to a subject comprising a therapeutically effective amount of at least one compound of Formula I, or individual isomers, racemic or non-racemic mixtures of isomers, or pharmaceutically acceptable salts or solvates thereof, in admixture with at least one suitable carrier.

This invention further relates to methods of treatment comprising administering to a subject in need of such treatment a therapeutically effective amount of a compound of Formula I, or individual isomers, racemic or non-racemic mixtures of isomers, or pharmaceutically acceptable salts or solvates thereof. In a preferred embodiment, the compound of Formula I, or individual isomers, racemic or non-racemic mixtures of isomers, or pharmaceutically acceptable salts or solvates thereof, is a 5-HT$_4$ receptor modulator, particularly a 5-HT$_4$ receptor antagonist. In another preferred embodiment, the subject in need of such treatment suffers from a disease state associated with a urinary tract disease state, a CNS disease state, a gastrointestinal disease state, or a cardiovascular disease state. In a more preferred embodiment, the subject in need of such treatment suffers from a urinary tract disease state. In a most preferred embodiment, the subject has a urinary tract disease state which is overactive bladder, outlet obstruction, outlet insufficiency, or pelvic hypersensitivity.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a," "an" and "the" include plural referents unless the context clearly dictates otherwise.

"Alkyl" means the monovalent branched or unbranched saturated hydrocarbon radical consisting solely of carbon and hydrogen atoms, having from one to twelve carbon atoms inclusive, unless otherwise indicated. Examples of alkyl radicals include, but are not limited to, methyl, ethyl, propyl, isopropyl, butyl, isobutyl, sec-butyl, tert-butyl, pentyl, n-hexyl, octyl, dodecyl, and the like.

"Lower alkyl" means the monovalent linear or branched saturated hydrocarbon radical, consisting solely of carbon and hydrogen atoms, having from one to six carbon atoms inclusive, unless otherwise indicated. Examples of lower alkyl radicals include, but are not limited to, methyl, ethyl, propyl, isopropyl, sec-butyl, tert-butyl, n-butyl, n-pentyl, n-hexyl, and the like.

"Cycloalkyl" means the monovalent saturated carbocyclic radical consisting of one or more rings, which can optionally be substituted with hydroxy, cyano, alkyl, alkoxy, thioalkyl, halogen, haloalkyl, hydroxyalkyl, nitro, alkoxycarbonyl, amino, alkylamino, dialkylamino, aminocarbonyl, carbonylamino, aminosulfonyl, sulfonylamino, and/or trifluoromethyl, unless otherwise indicated. Examples of cycloalkyl radicals include, but are not limited to, cyclopropyl, cyclobutyl, 3-ethylcyclobutyl, cyclopentyl, cyclohexyl, cycloheptyl, and the like.

"Alkoxy" means the radical —OR wherein R is lower alkyl as defined herein. Examples of alkoxy radicals include, but are not limited to, methoxy, ethoxy, isopropoxy, secbutoxy, isobutoxy, and the like.

"Aryl" means the monovalent monocyclic aromatic hydrocarbon radical consisting of one or more fused rings in which at least one ring is aromatic in nature, which can optionally be substituted with hydroxy, cyano, lower alkyl, lower alkoxy, thioalkyl, halogen, haloalkyl, hydroxyalkyl, nitro, alkoxycarbonyl, amino, alkylamino, dialkylamino, aminocarbonyl, carbonylamino, aminosulfonyl, sulfonylamino, and/or trifluoromethyl, unless otherwise indicated. Examples of aryl radicals include, but are not limited to, phenyl, naphthyl, biphenyl, indanyl, anthraquinolyl, and the like.

"Aryloxy" means the radical —OR wherein R is an aryl radical as defined herein. Examples of aryloxy radicals include, but are not limited to, phenoxy and the like.

"Heteroaryl" means the monovalent aromatic carbocyclic radical having one or more rings incorporating one, two, or three heteroatoms within the ring (chosen from nitrogen, oxygen, or sulfur) which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino and/or trifluoromethyl, unless otherwise indicated. Examples of heteroaryl radicals include, but are not limited to, imidazolyl, oxazolyl, pyrazinyl, thiophenyl, quinolyl, benzofuryl, pyridiyl, indolyl, pyrrolyl, pyranyl, naphtyridinyl, and the like.

"Heterocyclyl" means the monovalent saturated carbocyclic radical, consisting of one or more rings, incorporating one, two, or three heteroatoms (chosen from nitrogen, oxygen or sulfur), which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino and/or trifluoromethyl, unless otherwise indicated. Examples of heterocyclic radicals include, but are not limited to, morpholinyl, piperazinyl, piperidinyl, pyrrolidinyl, tetrahydropyranyl, thiomorpholinyl, and the like.

"Halogen" means the radical fluoro, bromo, chloro and/or iodo.

"Inert organic solvent" or "inert solvent" means a solvent inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methylethyl ketone, methanol, ethanol, propanol, isopropanol, tert-butanol, dioxane, pyridine, and the like. Unless specified to the contrary, the solvents used in the reactions of the present invention are inert solvents.

"Leaving group" means the group with the meaning conventionally associated with it in synthetic organic chemistry, i.e., an atom or group displaceable under alkylating conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Protective group" or "protecting group" has the meaning conventionally associated with it in synthetic organic chemistry, i.e., a group which selectively blocks one reactive site in a multifunctional compound such that a chemical reaction can be carried out selectively at another unprotective reactive site. Certain processes of this invention rely upon the protective groups intended to protect the nitrogen atom against undesirable reactions during synthetic procedures and includes, but is not limited to, acetyl, benzyl, benzyloxycarbonyl (carbobenzyloxy, CBZ), p-methoxybenzyloxy-carbonyl, N-tert-butoxycarbonyl (BOC), trifluoromethylcarbonyl, p-nitrobenzyloxy-carbonyl, and the like. It is preferred to use BOC or CBZ as the amino-protecting group because of the relative ease of removal, for example by mild acids in the case of BOC, e.g., trifluoroacetic acid or hydrochloric acid in ethyl acetate; or by catalytic hydrogenation in the case of CBZ.

"Deprotection" or "deprotecting" means the process by which a protective group is removed after the selective reaction is completed. Certain protective groups may be preferred over others due to their convenience or relative ease of removal.

"Optional" or "optionally" means that the subsequently described event or circumstance may but need not occur, and that the description includes instances where the event or circumstance occurs and instances in which it does not. For example, "optional bond" means that the bond may or may not be present and that the description includes both single and double bonds.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R- or S-) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al. *Angew. Chem. Inter*. Edit. 1966, 5, 385; errata 511; Cahn et al. *Angew. Chem*. 1966, 78, 413; Cahn and Ingold *J. Chem. Soc*. (London) 1951, 612; Cahn et al. *Experientia* 1956, 12, 81; Cahn, *J. Chem. Educ*. 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-lngold-Prelog rules.

"Atropic isomers" means the isomers owing their existence to restricted rotation caused by hindrance of rotation of large groups about a central bond.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable carrier" means a carrier that is useful in preparing a pharmaceutical composition that is generally compatible with the other ingredients of the composition, not deleterious to the recipient, and neither biologically nor otherwise undesirable, and includes a carrier that is acceptable for veterinary use as well as human pharmaceutical use. "A pharmaceutically acceptable carrier" as used in the specification and claims includes both one and more than one such carrier.

"Pharmaceutically acceptable salt" of a compound means a salt that is pharmaceutically acceptable and that possesses the desired pharmacological activity of the parent compound. Such salts, for example, include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-napthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like;

(2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like;

(3) internal salts formed when one or several nitrogen atoms of aliphatic or aromatic amines are oxidated to the N-oxide form such as N-oxides, in particular those N-oxides formed upon the oxidation of tertiary cyclic amines to give a chemically stable tertiary cyclic amine N-oxides, e.g., the piperidine N-oxide.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

"Subject" means mammals and non-mammals. Examples of mammals include, but are not limited to, any member of the Mammalia class: humans, non-human primates such as chimpanzees and other apes and monkey species; farm animals such as cattle, horses, sheep, goats, swine; domestic animals such as rabbits, dogs and cats; laboratory animals including rodents, such as rats, mice, and guinea pigs, and the like. Examples of non-mammals include, but are not limited to birds, and the like. The term does not denote a particular age or sex.

"Treating" or "treatment" of a disease state includes:

(1) preventing the disease state, i.e., causing the clinical symptoms of the disease state not to develop in a subject that may be exposed to or predisposed to the disease state but does not yet experience or display symptoms of the disease, (2) inhibiting the disease state, i.e., arresting the development of the disease state or its clinical symptoms, or (3) relieving the disease state, i.e., causing temporary or permanent regression of the disease state or its clinical symptoms.

A "therapeutically effective amount" means the amount of a compound that, when administered to a subject for treating a disease state, is sufficient to effect such treatment for the disease state. The "therapeutically effective amount" will vary depending on the compound, the disease state being treated, the severity of the disease state treated, the age and relative health of the subject, the route and form of administration, the judgement of the attending medical practitioner, and other factors.

"Pharmacological effect" encompasses effects produced in the subject that achieve the intended purpose of a therapy. In a preferred embodiment, a pharmacological effect means the treatment of a subject in need of such treatment. For example a pharmacological effect would be one that results in the prevention, alleviation, or reduction of a disease state associated with a urinary tract disease state, a CNS disease state, a gastrointestinal disease state, or a cardiovascular disease state.

"Modulator" means a molecule, such as a compound, that interacts with a target. The interactions include, but are not limited to, agonist, antagonist, and the like, as defined herein.

"Antagonist" means a molecule such as a compound, a drug, an enzyme inhibitor, or a hormone, that diminishes or prevents the action of another molecule or receptor site.

"Agonist" means a molecule, such as a compound, a drug, an enzyme activator or a hormone, that enhances the activity of another molecule or receptor site.

"Disease state" means any disease, disorder, condition, symptom, or indication.

"Disease states associated with the urinary tract" or "urinary tract disease state" or "uropathy" used interchangeably with "symptoms of the urinary tract" means the pathologic changes in the urinary tract, or dysfunction of urinary bladder smooth muscle or its innervation causing disordered urinary storage or voiding. Symptoms of the urinary tract include (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), and detrusor instability.

"Outlet obstruction" includes, but is not limited to, benign prostatic hypertrophy (BPH), urethral stricture disease, tumors, low flow rates, difficulty in initiating urination, urgency, and suprapubic pain.

"Outlet insufficiency" includes, but is not limited to, urethral hypermobility, intrinsic sphincteric deficiency, mixed incontinence, and stress incontinence.

"Pelvic Hypersensitivity" includes but is not limited to pelvic pain, interstitial (cell) cystitis, prostadynia, prostatis, vulvadynia, urethritis, orchidalgia, and overactive bladder.

"Disease states associated with the Central Nervous System (CNS)" or "CNS disease state" means neurological and/or psychiatric changes in the CNS, e.g., brain and spinal cord, which manifest in a variety of symptoms. Examples of CNS disease states, include, but are not limited to, migraine headache; cerebrovascular deficiency; psychoses including paranoia, schizophrenia, attention deficiency, and autism; obsessive/compulsive disorders including anorexia and bulimia; convulsive disorders including epilepsy and withdrawal from addictive substances; cognitive diseases including Parkinson's disease and dementia; and anxiety/depression disorders such as anticipatory anxiety (e.g., prior to surgery, dental work, etc.), depression, mania, seasonal affective disorder (SAD), and the convulsions and anxiety caused by withdrawal from addictive substances such as opiates, benzodiazepines, nicotine, alcohol, cocaine and other substances of abuse; and improper thermoregulation.

"Disease states associated with the gastrointestinal system (GI)" or "GI disease state" means physiological changes in the alimentary tract. Examples of GI disease states, include, but are not limited to, dyspepsia, gastric stasis, peptic ulcer, reflux esophagitis, bile reflux gastritis, pseudo-obstruction syndrome, diverticulitis, irritable bowel syndrome (IBS), inflammatory bowel disease, Crohn's disease, flatulence, biliary dysmotility, gastroparesis, retarded gastric emptying, chronic and acute diarrhea, diarrhea induced by cholera and carcinoid syndrome, and disturbed colonic motility. Other uses include short-term prokinesis to facilitate diagnostic radiology and intestinal intubation.

"Disease states associated with the cardiovascular system (CV)" or "CV disease state" means a physiological or pathological alteration in the cardiovascular system, in particular, improper cardiac chronotropy or arrhythmia. Examples of CV disease states, include, but are not limited to, bradyarrhythmia, tachyarrhythmia, supraventricular arrhythmia, atrial fibrillation, atrial flutter, or atrial tachycardia.

Nomenclature

The naming and numbering of the compounds of this invention is illustrated below:

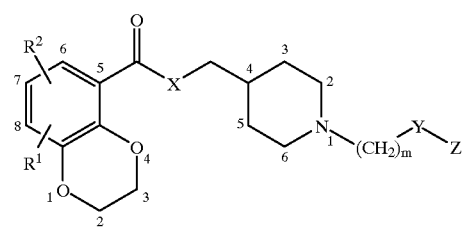

I

The side chains of the Z substituent are numbered as shown below:

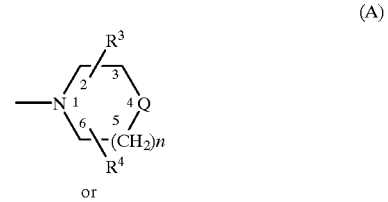

(A)

or

-continued

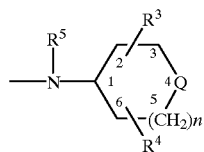
(B)

In general, the nomenclature used in this Application is generally based on AutoNom, a Beilstein Institute computerized system for the generation of IUPAC systematic nomenclature. However, because a strict adherence to these recommendations would result in the names changing substantially when only a single substituent is changed, compounds have been named in a manner that maintains consistency of nomenclature for the basic molecule.

For example, a compound of Formula I wherein X is —NH, Y is —SO$_2$, m is 3, and Z is represented by formula (A) wherein Q is —NR$^6$, n is 1, and R$^1$, R$^2$, R$^3$ and R$^4$ are each independently hydrogen, and R$^6$ is methyl, is named 2,3-dihydrobenzo[1,4]-dioxine-5-carboxylic acid {1-[3-(4-methylpiperazine-1-sulfonyl)propyl]piperidin-4-ylmethyl}amide.

For example, a compound of Formula I wherein X is —CH$_2$, Y is —SO$_2$, m is 3, and Z is represented by formula (A) wherein Q is O, n is 1, and R$^1$, R$^2$, R$^3$ and R$^4$ are each independently hydrogen, is named 1-(2,3-dihydrobenzo[1,4]dioxin-5-yl)-3-{1-3-(morpholine-4-sulfonyl)propyl]piperidin-4-yl}propan-1-one.

Preferred Compounds

Among the compounds of the present invention set forth in the Summary of the Invention, certain compounds of Formula I, or individual isomers, racemic or non-racemic mixtures of isomers, or pharmaceutically acceptable salts or solvates thereof, are preferred wherein:

R$^1$ and R$^2$ are each independently in each occurrence preferably hydrogen;

X is independently in each occurrence preferably —NH;

m is independently in each occurrence preferably an integer 3;

Y is independently in each occurrence preferably —SO$_2$;

Z is independently in each occurrence preferably formula (A):

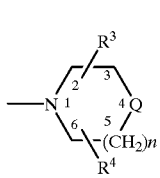
(A)

wherein:
R$^3$ and R$^4$ are each independently in each occurrence preferably hydrogen;
Q is independently in each occurrence preferably O, —NR$^6$, or —CR$^7$R$^8$, more preferably —NR$^6$;
n is independently in each occurrence preferably an integer 1;
wherein:
R$^6$ is independently in each occurrence preferably lower alkyl, cycloalkyl, —SO$_2$R$^9$, or aryl optionally mono- or di-substituted with halogen or lower alkyl;

R$^7$ is independently in each occurrence preferably hydrogen;
R$^8$ is independently in each occurrence preferably hydrogen, or lower alkyl, or R$^7$ and R$^8$ taken together with the common ring carbon to which they are attached form a monocyclic saturated 5- or 6-membered ring optionally independently containing 0 or 1 heteroatom of nitrogen, oxygen, or sulfur.
wherein:
p is independently in each occurrence preferably an integer 0 or 1, more preferably 0;
R$^9$ is independently in each occurrence preferably lower alkyl or aryl optionally mono- or di-substituted with halogen or lower alkyl;
R$^{10}$ and R$^{11}$ are each independently in each occurrence preferably hydrogen.

Among the compounds of the present invention set forth in the Summary of the Invention, one preferred group of compounds of Formula I, designated "Group A", are those compounds wherein:

R$^1$ and R$^2$ are each independently hydrogen;
m is 3;
X is —NH; and
Z is formula (A), n is 1, and R$^3$ and R$^4$ are each independently hydrogen.

A first preferred subgroup among the Group A compounds are those compounds wherein:

Q is —NR$^6$ wherein:
R$^6$ is lower alkyl, cycloalkyl, aryl optionally mono- or di-substituted with halogen, or —SO$_2$R$^9$, more preferably methyl, ethyl, propyl, isopropyl, butyl, isobutyl, cyclopentyl; or phenyl, 4-fluorophenyl or 4-chlorophenyl, most preferably methyl;
R$^9$ is lower alkyl, or aryl optionally mono- or di-substituted with halogen; more preferably methyl, ethyl, propyl, isopropyl, butyl, isobutyl, phenyl, 4-fluorophenyl, or 4-chlorophenyl.

A second preferred subgroup among the Group A compounds are those compounds wherein:

Q is —CR$^7$R$^8$ wherein:
R$^7$ and R$^8$ are each independently hydrogen or lower alkyl, more preferably hydrogen, methyl, ethyl, or propyl; or
R$^7$ and R$^8$ taken together with the common ring carbon to which they are attached form a monocyclic saturated 5- or 6-membered ring optionally containing 0, or 1 heteroatom of nitrogen, oxygen, or sulfur; more preferably R$^7$ and R$^8$ taken together with the common ring carbon to which they are attached form a monocyclic saturated 5-membered ring containing 0 hetero-atoms.

Another preferred group of compounds of Formula I, designated "Group B", are those compounds wherein R$^1$ and R$^2$ are each independently hydrogen; Y is —SO$_2$, and m is 3; X is —CH$_2$; Z is formula (A), n is 1, and R$^3$ and R$^4$ are each independently hydrogen; and Q is O.

It is understood that the preferred compounds of Formula I designated groups A and B above also include individual isomers, racemic or non-racemic mixtures of isomers, or pharmaceutically acceptable salts or solvates thereof. Exemplary particularly preferred compounds include the following compounds of Formula I, or individual isomers, racemic or non-racemic mixtures of isomers, or pharmaceutically acceptable salts or solvates thereof:

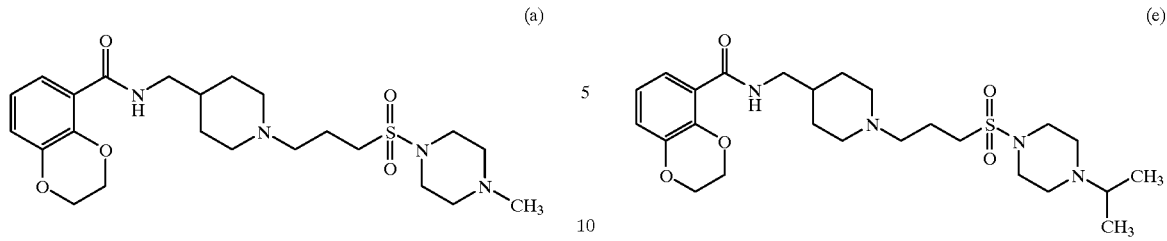

(a) 2,3-dihydrobenzo[1,4]dioxine-5-carboxylic acid{1-[3-(4-methylpiperazine-1-sulfonyl)propyl]piperidin-4-ylmethyl}amide;

(b) 2,3-dihydrobenzo[1,4]dioxine-5-carboxylic acid{1-[3-(4-propylpiperidine-1-sulfonyl)propyl]piperidin-4-ylmethyl}amide;

(c) 2,3-dihydrobenzo[1,4]dioxine-5-carboxylic acid{1-[3-(4-propylpiperazine-1-sulfonyl)propyl]piperidin-4-ylmethyl}amide;

(d) 2,3-dihydrobenzo[1,4]dioxine-5-carboxylic acid(1-{3-[4-[(4-fluorophenyl)piperazine-1-sulfonyl]-propyl}piperidin-4-ylmethyl)amide;

(e) 2,3-dihydrobenzo[1,4]dioxine-5-carboxylic acid{1-[3-(4-isopropylpiperazine-1-sulfonyl)propyl]piperidin-4-ylmethyl}amide;

(f) 2,3-dihydrobenzo[1,4]dioxine-5-carboxylic acid{1-[3-(4-cyclopentylpiperazine-1-sulfonyl)propyl]piperidin-4-ylmethyl}amide;

(g) 2,3-dihydrobenzo[1,4]dioxine-5-carboxylic acid{1-[3-(8-azaspiro[4.5]decane-8-sulfonyl)propyl]piperidin-4-ylmethyl}amide;

(h) 2,3-dihydrobenzo[1,4]dioxine-5-carboxylic acid(1-{3-[4-(4-fluorobenzenesulfonyl)piperazine-1-sulfonyl]propyl}piperidin-4-ylmethyl)amide;

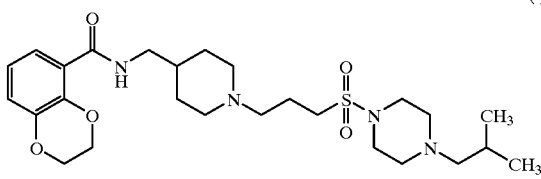

2,3-dihydrobenzo[1,4]dioxine-5-carboxylic acid{1-[3-(4-isobutylpiperazine-1-sulfonyl)propyl]piperidin-4-ylmethyl}amide;

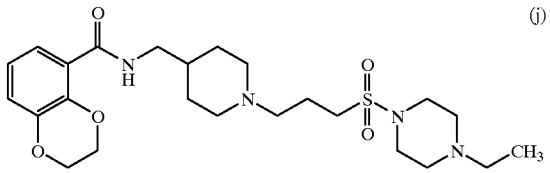

2,3-dihydrobenzo[1,4]dioxine-5-carboxylic acid{1-[3-(4-ethylpiperazine-1-sulfonyl)propyl]piperidin-4-ylmethyl}amide; and

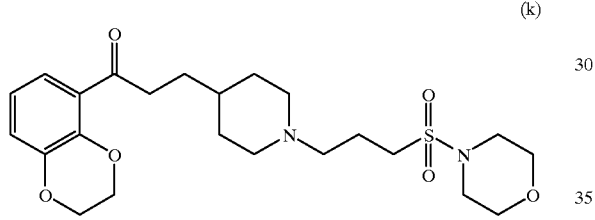

1-(2,3-dihydrobenzo[1,4]dioxin-5-yl) 3-{1-[3-(morpholine-4-sulfonyl)propyl]piperidin-4-yl}propan-1-one.

GENERAL SYNTHETIC SCHEME

Compounds of this invention may be made by the methods depicted in the reaction schemes shown below.

The starting materials and reagents used in preparing these compounds are either available from commercial suppliers such as Aldrich Chemical Co. or are prepared by methods known to those skilled in the art following procedures set forth in references such as *Fieser and Fieser's Reagents for Organic Synthesis*, Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C., and conveniently at about room (or ambient) temperature, e.g., about 20° C.

Schemes A, B, C, and D describe alternative methods to generate the compounds of Formula I.

Scheme A

Scheme A, in general, describes a method of preparing compounds of Formula I wherein X, Y, and Z are as defined in the Summary of the Invention.

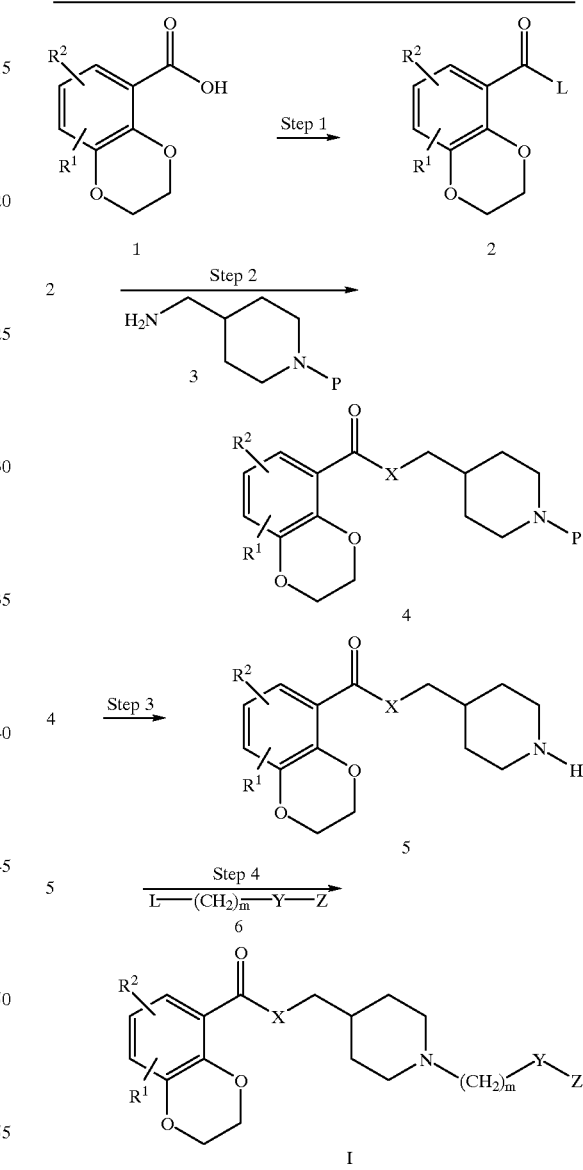

In general, the starting compounds of 2,3-dihydrobenzo[1,4]dioxine-5-carboxylic acid 1, an activated carboxylic acid derivative 2, and a protected (aminomethyl)piperidine 3 wherein P is a suitable protecting group such as benzyl, tert-butoxycarbonyl (BOC) or carbobenzyloxy (CBZ), preferably BOC, are commercially available or known to or can readily be synthesized by those of ordinary skill in the art. For example, compound 1 can be prepared by the method described in Fuson et al., *J. Org. Chem.* 1948, 13, 494;

compound 3 wherein P is BOC, can be prepared by the method described in Prugh et al., *Synthetic Commun.* 1992, 22, 2357.

In step 1, an activated carboxylic acid derivative 2 wherein L is a leaving group such as chloro, is prepared by treating the compound 1 with a suitable chlorinating agent, e.g., thionyl chloride or oxalyl chloride, under conditions well known to one skilled in the art. Suitable solvents for the reaction include aprotic organic solvents such as dichloromethane, chloroform, dichloromethane, 1,2-dichloroethane or tetrahydrofuran, and the like.

In step 2, a protected (piperidin-4-ylmethyl)amide 4 wherein P is a suitable protecting group, preferably BOC, is prepared by reacting compound 2 with a protected (aminomethyl)piperidine 3 under acylating conditions. The reaction proceeds in the presence of base such as triethylamine in a suitable inert organic solvent, for example dichloromethane, 1,2-dichlorethane, chloroform, tetrahydrofuran, and the like.

In step 3, a deprotected (piperidin-4-ylmethyl)amide 5 is prepared by removing the protecting group from compound 4 by methods known to one of ordinary skill in the art. For example, when the protecting group is BOC, the deprotecting reaction proceeds by treatment with a strong organic acid such as trifluroacetic acid in an inert organic solvent such as halogenated hydrocarbons including dichloromethane or 1,2-dichloroethane. For example, the deprotecting reaction may also proceed by warming compound 4 in an 10% ethanolic hydrochloric acid solution.

In step 4, a compound of Formula I is prepared by reacting compound 5 with an alkylating agent 6 wherein L is a leaving group, particularly halogen, under alkylating conditions. The alkylating reaction proceeds in the presence of a base such as triethylamine and a catalyst such as sodium iodide. Suitable solvents for the reaction include aprotic organic solvents such as tetrahydrofuran, N,N-dimethylformamide, acetonitrile, dimethyl sulfoxide, 1-methyl-2-pyrrolidinone, and the like.

Exemplary preparations of the following compounds utilizing the reaction conditions described in Scheme A are given. A compound of formula 4 is described in Preparation 2, a compound of formula 5 is described in detail in Preparation 3A, a compound of formula 6 is described in Preparation 4, and a compound of Formula I is described in Example 1.

Scheme B

Scheme B describes an alternative method of preparing compounds of Formula I, in particular wherein X is ——NH, Y is as described in the Summary of the Invention, and Z is represented by formula (A) wherein Q is ——NR⁶ and R⁶ is as described in the Summary of the Invention.

Alternative Step 4

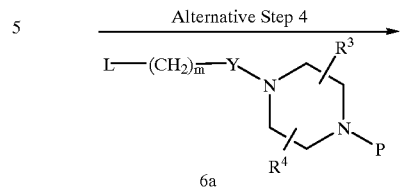

6a

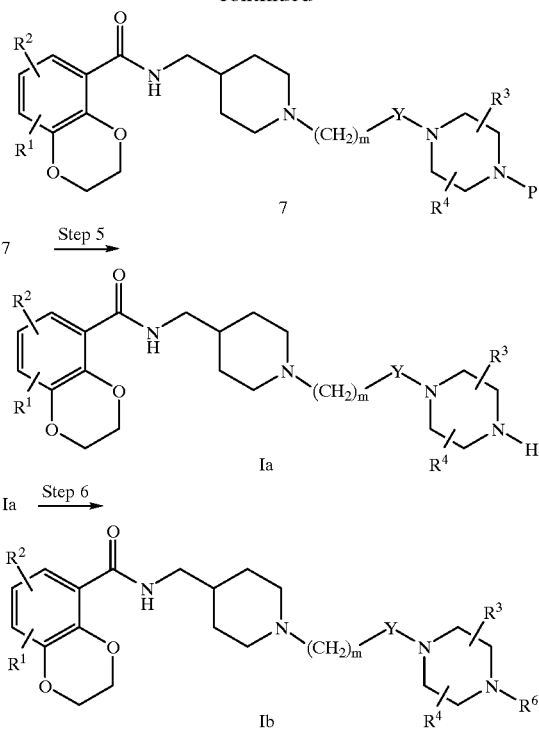

Alternatively, a compound of Formula Ia or Ib can be prepared by utilizing the reaction conditions previously described in Scheme A, but substituting step 4 in Scheme A with alternative step 4 in Scheme B, and proceeding as in Scheme B above.

In alternative step 4, a protected piperazine compound 7 wherein P is a suitable protecting group, is prepared by reacting compound 5 with a protected alkylating agent 6a wherein L is a leaving group, particularly halogen, under alkylating conditions. The alkylating reaction proceeds in the same manner as described in Scheme A, step 4.

In step 5, a compound of Formula Ia is prepared by removing the protecting group from compound 7 by methods known to one of ordinary skill in the art. For example, when the protecting group is BOC, the deprotecting reaction proceeds in the same manner as described in Scheme A, step 3.

Optionally, in step 6, a compound of Formula Ib can be prepared by treating a compound of Formula Ia with an alkylating agent R⁶L wherein R⁶ is other than hydrogen and L is a leaving group such as halogen, under alkylating conditions, as described in Scheme A, step 4.

Exemplary preparations of the following compounds utilizing the reaction conditions described in Scheme B are given. Exemplary preparations of a compound of formula 6a is described in detail in Preparation 5, a compound of Formula Ia is described in detail in Example 2, and a compound of Formula Ib is described in Examples 4 and 5.

Scheme C

Scheme C describes an alternative method of preparing compounds of Formula I, in particular wherein X is —NH, Y is as described in the Summary of the Invention, and Z is represented by formula (A), and particularly wherein Q is —NR⁶ and R⁶ is hydrogen.

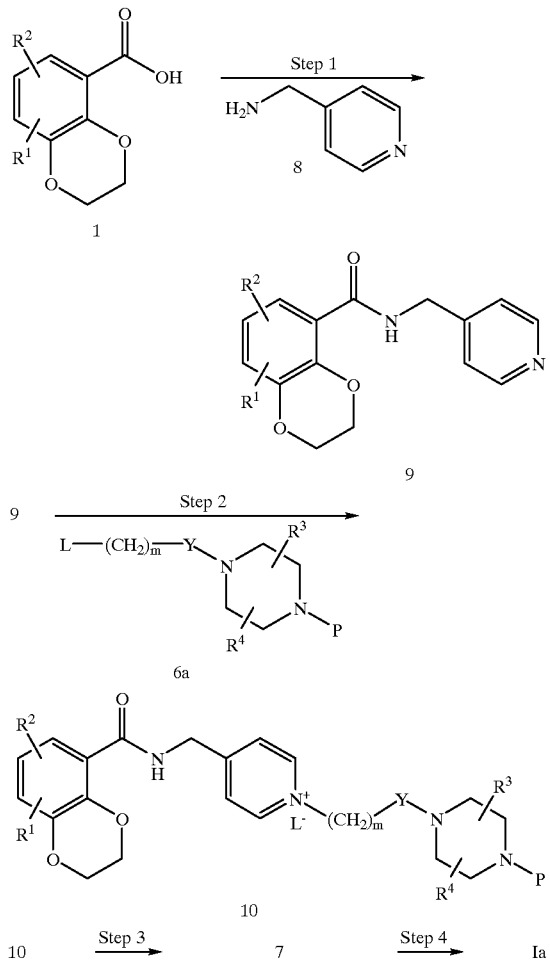

The starting compounds of formula 1 and an (aminomethyl)pyridine 8 are commercially available, for example from Aldrich Chemical Company, or known to or can readily be synthesized by those of ordinary skill in the art.

In step 1, a (pyridin-4-ylmethyl)amide 9 is prepared by acylating the (pyridin-4-ylmethyl)amine 8 with a carboxylic acid 1 in the presence of a coupling agent such as N,N'-carbonyidiimidazole (CDI), dicylohexyl-carbodiimide (DCC) or 1-(3-dimethylaminopropyl)-3-ethylcarbodiimide (EDCI). Suitable solvents for the reaction include aprotic organic solvents such as tetrahydrofuran, N,N-dimethylforamide, and the like.

In step 2, a pyridinium salt 10 is prepared by reacting compound 9 with a protected alkylating agent 6a wherein L is a leaving group, particularly halogen, under alkylating conditions previously described in Scheme A, step 4.

In step 3, the piperidinyl compound 7 is prepared by the reduction of compound 10. Suitable pyridinyl reducing conditions include catalytic hydrogenation, for example Raney nickel, or platinum or palladium catalyst, (e.g., PtO₂ or Pd/C) in a protic organic solvent such as methanol or ethanol.

In step 4, a compound of Formula Ia is prepared from compound 8 utilizing the methods described in Scheme B.

Exemplary preparations of the following compounds utilizing the reaction conditions described in Scheme C are given. Exemplary preparations of a compound of formula 6a is described in detail in Preparation 5, a compound of formula 9 is described in detail in Preparation 7A, and a compound of Formula Ia is described in detail in Example 3.

Scheme D

Scheme D describes an alternative method of preparing compounds of Formula I, in particular wherein X is —NH, Y is as described in the Summary of the Invention, and Z is represented by formula (A), and particulary wherein Q is —NR⁶ and R⁶ is other than hydrogen.

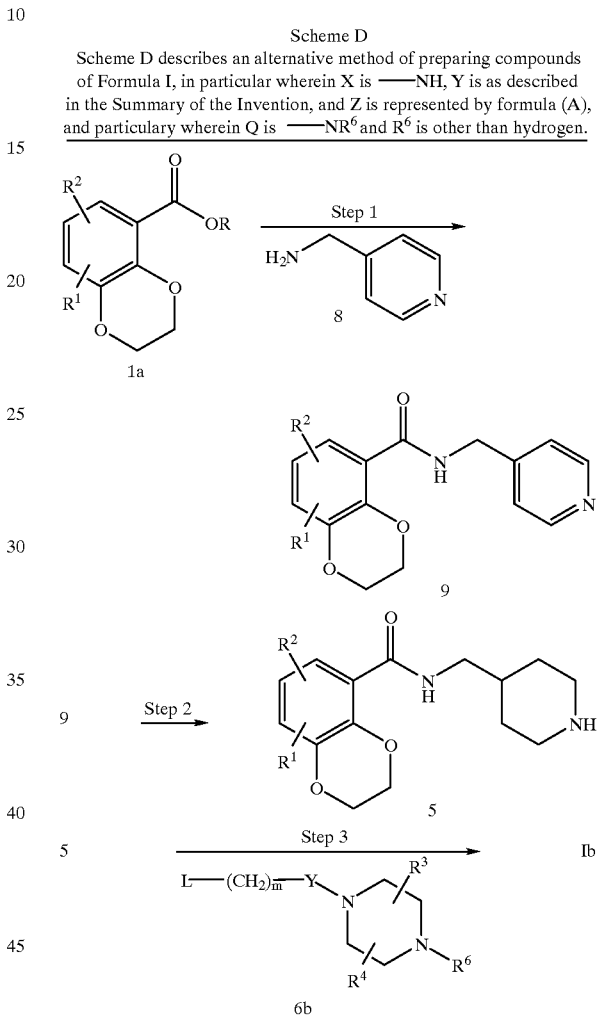

The starting compounds of carboxylic acid ester 1a and (aminomethyl)pyridine 8 are commercially available, or known to or can readily be synthesized by those of ordinary skill in the art. For example, the carboxylic acid ester 1a can be prepared by methods known in the art such as by the esterification of the corresponding carboxylic acid, or by the esterification of a 2,3-dihydroxybenzoic acid, and subsequent cyclization of the 2,3-dihydroxybenzoic benzoic acid ester in a suitable solvent such as 1,2-dichloroethane under phase-transfer reaction conditions.

In step 1, a (pyridin-4-ylmethyl)amide 9 is prepared by acylating a (pyridin-4-ylmethyl)amine 8 with a carboxylic acid ester 1a in the presence a strong base such as sodium methoxide in a suitable protic organic solvent such as methanol.

In step 2, a (piperidin-4-ylmethyl)amide 5 is prepared by reducing the pyridinyl group of compound 9 to a piperidinyl group. Suitable pyridinyl reducing conditions include catalytic hydrogenation, for example Raney nickel, or platinum or palladium catalyst, (e.g., $PtO_2$ or Pd/C) in a protic organic solvent such as methanol or ethanol.

Alternatively, a (piperidin-4-ylmethyl)amide 5 can be prepared by treating the carboxylic acid ester 1a with a lithiated (aminomethyl)piperidine (prepared by treating the (aminomethyl)piperidine with an organometallic reagent such as n-butyllithium in an aprotic solvent such as tetrahydrofuran under conditions well known in the art). The reaction proceeds at a temperature of about 25° to 100° C.

Alternatively, a (piperidin-4-ylmethyl)amide 5 can be prepared by treating the carboxylic acid ester 1a with an (aminomethyl)piperidine in the presence of a strong base such as sodium methoxide in a protic organic solvent such as methanol.

In step 3, a compound of Formula Ib is prepared by treating compound 5 with an alkylating agent 6a wherein L is a leaving group, particularly halogen, under alkylating conditions. The reaction proceeds under phase transfer conditions in the presence of a base such as potassium carbonate, sodium carbonate, sodium hydroxide, or trisodium phosphate, a phase transfer catalyst such as tetra-n-butylammonium bromide, and a reaction enhancer such as potassium bromide. Preferable solvent systems for the reaction include toluene/water and the like.

Exemplary preparations of the following compounds utilizing the reaction conditions described in Scheme D are given. Exemplary preparations of a compound of formula 1a is described in detail in Preparation 1, a compound of formula 5 is described in detail in Preparation 3B, 3C, and 3D, a compound of formula 6b is described in detail in Preparation 6, a compound of formula 9 is described in detail in Preparation 7B, and a compound of Formula Ib is described in detail in Example 6.

Scheme E
Scheme E describes an alternative method of preparing compounds of Formula I, in particular wherein X is ——$CH_2$,Y and Z are as described in the Summary of the Invention.

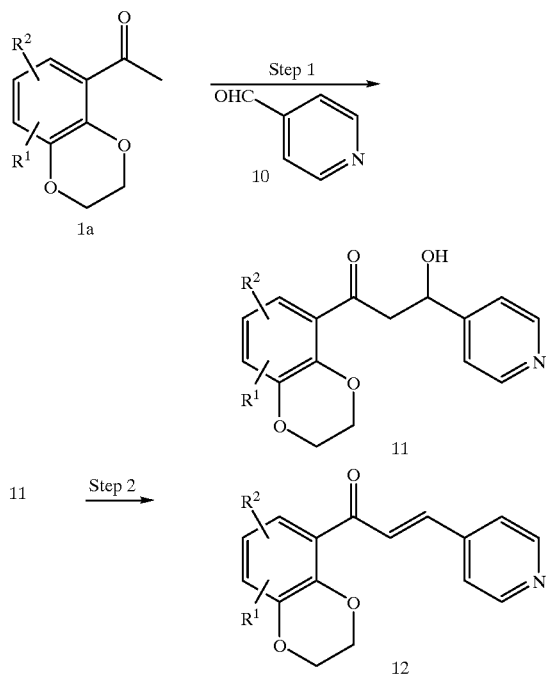

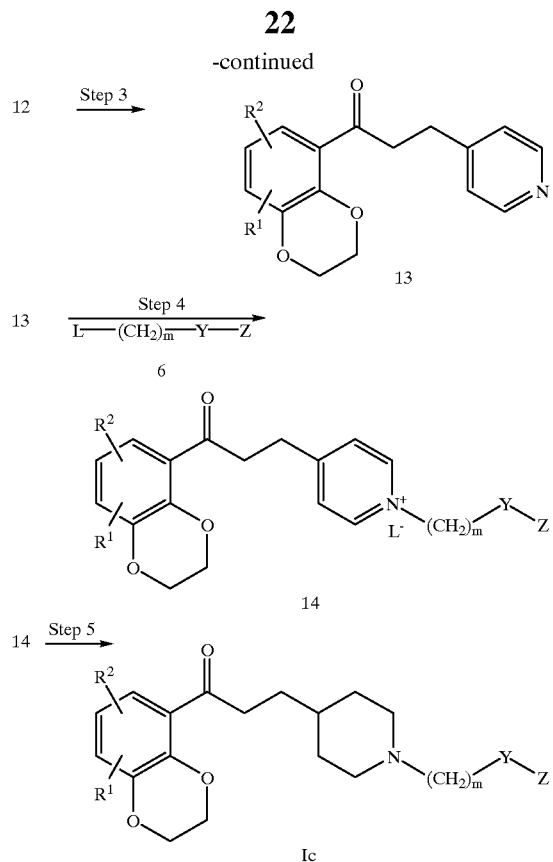

The starting compound of a (2,3-dihydrobenzo[1,4]dioxin-5-yl) ketone 1a can readily be synthesized from 2,3-dihydrobenzo[1,4]dioxine by methods known to one of ordinary skill in the art, for example, by methods similarly described U.S. Pat. No. 5,763,458.

The starting compound of pyridine-4-carboxaldehyde 10 is commercially available, for example, from Aldrich Chemical Company, or known to or can readily be synthesized by those of ordinary skill in the art.

In step 1, a pyridinyl β-hydroxy ketone 11 is prepared by reacting compound 1a with compound 10 under aldol condensation reaction conditions, preferably in the presence of a base such as lithium diisopropylamide. The reaction proceeds at a reduced temperature of about −20° to 0° C. in a suitable aprotic organic solvent such as tetrahydrofuran, diethyl ether, and the like.

In step 2, a pyridinyl enone 12 is prepared by dehydrating the alcohol group of compound 14 to an alkene group under conditions well known to one skilled in the art. The elimination reaction proceeds in the presence of an acid such as sulfuric acid, hydrochloric acid, or a Lewis acid.

In step 3, a pyridinyl ketone 13 is prepared by the hydrogenation of the alkene group of compound 12 to an alkyl group under conditions well known to one skilled in the art. Suitable hydrogenation conditions include catalytic hydrogenation using a platinum or palladium catalyst (e.g., $PtO_2$ or Pd/C) in a protic organic solvent such as methanol, ethanol, ethyl acetate, and the like.

In step 4, a pyridinium salt 14 is prepared by reacting compound 13 with an alkylating agent 6 wherein L is a leaving group, particularly halogen, under alkylating conditions previously described in Scheme A, step 4.

In step 5, a compound of Formula Ic is prepared by the reduction of pyridinyl group of compound 14 to a piperidinyl group. Suitable pyridinyl reducing conditions include catalytic hydrogenation, for example Raney nickel or platinum or palladium catalyst (e.g., $PtO_2$ or Pd/C) in an alcoholic solvent such as methanol or ethanol.

Exemplary preparations of the following compounds utilizing the reaction conditions described in Scheme E are given. A compound of formula 11 is described in Preparation 8, a compound of formula 12 is described in Preparation 9, a compound of formula 13 is described in Preparation 10, and a compound of Formula Ic is described in Example 7.

General Utility

The compounds of Formula I are $5-HT_4$ receptor modulators, in particular $5-HT_4$ antagonists, and as such possess selective antagonist activity at the $5-HT_4$ receptor. These compounds (and compositions containing them) are expected to be useful-in the prevention and treatment of a variety of diseases in mammals, especially humans. For example, the compounds of Formula I can block $5-HT_4$ receptor mediated peristalsis, mediated enhancement of neurogenic contractions of detrusor smooth muscle, or mediated positive chronotropy, and thus are useful in the treatment of a variety of disease states related directly or indirectly to urinary tract disease states, CNS disease states, gastrointestinal disease states, and cardiovascular disease states.

The compounds of this invention are expected to find utility in the treatment of disease states associated with the urinary tract including, but not limited to, overactive bladder, outlet obstruction, outlet insufficiency, and pelvic hypersensitivity (see Ford, A. P. D. W. and Kava, supra). In particular, the compounds of the present invention may be useful in the treatment of the following symptoms associated with the above disease state such as urgency, frequency, altered bladder capacity, incontinence, micturition threshold, unstable bladder contractions, sphincteric spasticity, detrusor hyperreflexia (neurogenic bladder), detrusor instability, benign prostatic hyperplasia (BPH), urethral stricture disease, tumors, low flow rates, difficulty in initiating urination, urgency, suprapubic pain, urethral hypermobility, intrinsic sphincteric deficiency, mixed incontinence, stress incontinence, pelvic pain, interstitial (cell) cystitis, prostadynia, prostatis, vulvadynia, urethritis, orchidalgia, and other symptoms related to overactive bladder.

Additionally, the compounds of the present invention are useful in treating a CNS disease state, including but not limited to, migraine headache; cerebrovascular deficiency; psychoses such as paranoia, schizophrenia, attention deficiency, and autism; obsessive/compulsive disorders such as anorexia and bulimia; convulsive disorders such as epilepsy and withdrawal from addictive substances; cognitive disorders such as Parkinson's disease and dementia; and anxiety/depression disorders such as anticipatory anxiety (e.g., prior to surgery, dental work, etc.), depression, mania, seasonal affective disorder (SAD), and the convulsions and anxiety caused by withdrawal from addictive substances such as opiates, benzodiazepines, nicotine, alcohol, cocaine and other substances of abuse; and improper thermoregulation.

The compounds of the present invention may also be useful in treating a gastrointestinal disease state including, but not limited to, dyspepsia, gastric stasis, peptic ulcer, reflux esophagitis, bile reflux gastritis, pseudo-obstruction syndrome, diverticulitis, irritable bowel syndrome, inflammatory bowel disease, Crohn's disease, flatulence, biliary dysmotility, gastroparesis, retarded gastric emptying, acute and chronic diarrhea, diarrhea induced by cholera or carcinoid syndrome, and disturbed colonic motility. Other uses include short-term prokinesis to facilitate diagnostic radiology and intestinal intubation.

The compounds of the present invention may also be useful in treating a cardiovascular disease states, including, but not limited to, bradyarrhythmia, supraventricular arrhythmia, atrial fibrillation, atrial flutter, and atrial tachycardia.

Testing

The $5-HT_4$ receptor antagonist activity of the test compounds can be identified by an in vitro assay which utilizes isolated thoracic esophagus muscle in the rat. This assay is well-established as a model for identifying and characterizing compounds that interact with $5-HT_4$ receptors (e.g., see Baxter, G. S. et al., *Naunyn-Schmiedeberg's Arch.Pharmacol*, 1991, 343, 439–446), and is described in more detail in Example 15.

The $5-HT_4$ receptor antagonist properties of the test compounds can be identified by an in vivo assay by determining the inhibitory activity on 5-HT induced heart rate increases in anesthetized and vagotomized Yucatan micropigs (e.g., see Eglen et al., *Br. J. Pharmacol*. 1993, 108, 376–382) and is described in more detail in Example 16.

Administration and Pharmaceutical Composition

The invention includes a pharmaceutical composition comprising a compound of the present invention or individual isomers, racemic or non-racemic mixture of isomers, or pharmaceutically acceptable salts or solvates thereof, together with one or more pharmaceutically acceptable carriers, and optionally other therapeutic and/or prophylactic ingredients.

In general, the compounds of this invention will be administered in a therapeutically effective amount by any of the accepted modes of administration for agents that serve similar utilities. Suitable dosage ranges are 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of this invention for a given disease.

In general, compounds of this invention will be administered as pharmaceutical formulations including those suitable for oral (including buccal and sub-lingual), rectal, nasal, topical, pulmonary, vaginal or parenteral (including intramuscular, intraarterial, intrathecal, subcutaneous and intravenous) administration or in a form suitable for administration by inhalation or insufflation. The preferred manner of administration is oral using a convenient daily dosage regimen which can be adjusted according to the degree of affliction.

The compounds of the invention, together with a conventional adjuvant, carrier, or diluent, may be placed into the form of pharmaceutical compositions and unit dosages. The pharmaceutical compositions and unit dosage forms may comprise of conventional ingredients in conventional proportions, with or without additional active compounds or principles, and the unit dosage forms may contain any suitable effective amount of the active ingredient commensurate with the intended daily dosage range to be employed. The pharmaceutical composition may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing one (1) milligram of active ingredient or, more broadly, 0.01 to one hundred (100) milligrams, per tablet, are accordingly suitable representative unit dosage forms.

The compounds of the present invention may be formulated in a wide variety of oral administration dosage forms. The pharmaceutical compositions and dosage forms may comprise the compounds of the invention or its pharmaceutically acceptable salt or a crystal form thereof as the active component. The pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is a mixture with the finely divided active component. In tablets, the active component is mixed with the carrier having the necessary binding capacity in suitable proportions and compacted in the shape and size desired. The powders and tablets preferably containing from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example with a dropper, pipette or spray. The formulations may be provided in a single or multidose form. In the latter case of a dropper or pipette this may be achieved by the patient administering an appropriate, predetermined volume of the solution or suspension. In the case of a spray this may be achieved for example by means of a metering atomizing spray pump.

The compounds of the present invention may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 8 to 14.

EXAMPLES

The following preparations and examples are given to enable those skilled in the art to more clearly understand and to practice the present invention. They should not be considered as limiting the scope of the invention, but merely as being illustrative and representative thereof.

PREPARATION 1

2,3-Dihydrobenzo[1,4]dioxin-5-carboxylic acid ethyl ester

The following is the preparation of a compound of formula 1a wherein $R^1$ and $R^2$ are each independently hydrogen, and R is ethyl.

A mixture of 2,3-dihydroxybenzoic acid(994 g), ethanol (3.8 L) and sulfuric acid (320 g) was refluxed for 44 hours. A portion of the solvent distilled out of the solution, and the solution was cooled and stirred overnight, and then further cooled in an ice/water bath. To the solution was added water (5.6 L). The solution was aged, and the crystals were filtered, washed with water, and dried to give ethyl 2,3-dihydroxybenzoate (1002 g, 85%); m.p. 66.0–67.2° C.

A mixture of ethyl 2,3-dihydroxybenzoate (1000 g), tetra-n-butyl-ammonium bromide (880 g), potassium carbonate (1552 g), 1,2-dichloroethane (3216 g), and water (10 kg) was refluxed for 5 hours. The solution was cooled and extracted with toluene. The extract was washed with a solution of 1N hydrochloric acid and sodium chloride. The solution was partially concentrated and filtered through silica gel (300 g). The filtrated was concentrated to give the title compound (1074 g, 94%); m.p. 48–51° C.

PREPARATION 2

4-{[(2,3-Dihydrobenzo[1,4]dioxin-5-carbonyl) amino]methyl}piperidine-1-carboxylic acid tert-butyl ester The following is the preparation of a compound of formula 4 wherein $R^1$ and $R^2$ are each hydrogen, X is —NH, and P is BOC.

A suspension of 2,3-dihydrobenzo[1,4]dioxine-5-carboxylic acid (prepared by the method described in Fuson et al., *J. Org. Chem.* 1948, 13, 494) (16.4 g, 100 mmol) in dichloromethane (100 mL) was treated with oxalyl chloride (10.8 mL, 125 mmol) and N,N-dimethylformamide (5 drops). The reaction mixture was stirred at room temperature for 4 hours and then concentrated in vacuo. The resulting crystalline acid chloride was dissolved in dichloromethane (250 mL), cooled in an ice-bath. Triethylamine (21 mL, 150 mmol) was added followed by dropwise addition of a solution of 4-(aminomethyl)-piperidine-1-carboxylic acid tert-butyl ester (prepared by the method described in Prugh et al., *Synthetic Commun.* 1992, 22, 2357) (21.4 g, 100 mmol). The stirred mixture was allowed to warm to room temperature over 2 hours and was then washed with water, dilute hydrochloric acid and brine, dried ($Na_2SO_4$) and evaporated in vacuo. The crude product was recrystallized from ethyl acetate-cyclohexane to give the title compound as a white solid (27.8 g, 76%); m.p. 103–105° C. Analysis for $C_{20}H_{28}N_2O_5$: Calcd.: C, 63.81; H, 7.50; N, 7.44. Found: C, 64.01; H, 7.50; N, 7.56.

PREPARATION 3

2,3-Dihydrobenzo[1,4]dioxine-5-carboxylic acid (piperidin-4-ylmethyl)amide

The following is the preparation of a compound of formula 5 wherein $R^1$ and $R^2$ are each hydrogen, and X is —NH.

A. A solution of the 4-{[(2,3-dihydrobenzo[1,4]dioxin-5-carbonyl)amino]-methyl}piperidine-1-carboxylic acid tert-butyl ester (36.6 g, 100 mmol) in dichloromethane (50 mL) was treated with trifluoroacetic acid (50 mL) and the resulting solution was stirred at room temperature for 1 hour. Copious amounts of gas were evolved. The mixture was concentrated in vacuo and the residue was partitioned between dichloromethane and brine, and the aqueous layer was basified by the addition of aqueous ammonium hydroxide. The layers were separated and the aqueous layer was extracted three times with dichloromethane. The combined dichloromethane extracts were dried ($Na_2SO_4$) and evaporated in vacuo to give the title compound as an amorphous powder (27 g, 98%). A hydrochloride salt was prepared from ethanol-ether; m.p. 216–217° C. Analysis for $C_{15}H_{20}N_2O_3 \cdot HCl \cdot 0.1\ H_2O$: Calcd.: C, 57.27; H, 6.79; N, 8.90. Found: C, 56.95; H, 6.79; N, 9.24.

B. A mixture of 2,3-dihydrobenzo[1,4]dioxine-5-carboxylic acid(pyridin-4-ylmethyl)amide (50 g), platinum oxide (1.26 g), isopropanol (300 mL), and concentrated hydrochloric acid (30.83 mL) was stirred at a temperature of 45 ° C. under a hydrogen atmosphere for 10 hours. The mixture was filtered, and the filtrate was diluted with isopropanol (350 mL) and concentrated. The concentrate was diluted with isopropanol (400 mL) and concentrated. The remaining solution was cooled slowly to −10° C., filtered, washed with cold isopropanol and hexanes, and dried to give the title compound (46 g, 80%); m.p. 201.9–202.5° C.

C. To a cooled solution of 4-(aminomethyl)piperidine (1053 g) in tetrahydrofuran (7 L) was slowly added a solution of n-butyllithium in hexanes (1.6M, 3.97 kg) and a solution of 2,3-dihydrobenzo[1,4]-dioxine-5-carboxylic acid ethyl ester (1067 g) dissolved in tetrahydrofuran (1.5 L). The reaction mixture was stirred in a cold bath for an hour and then at 40° C. for about a day, diluted with water (5 L), and concentrated. To the concentrate was slowly added concentrated hydrochloric acid (2.46 kg). The solution was washed with dichloromethane, and sodium hydroxide (50%, 1.53 kg) was added. The solution was extracted with dichloromethane, and the extract was washed with sodium hydroxide (1N, 2 L), dried (Na$_2$SO$_4$), filtered, and concentrated. The concentrate was diluted with toluene (10 L), concentrated, and slowly cooled to form crystals. The crystals were filtered, washed with toluene and dried to give the title compound (507 g, 40%).

D. A mixture of 2,3-dihydrobenzo[1,4]dioxine-5-carboxylic acid ethyl ester (1.7 g), toluene (5 mL), 4-(aminomethyl) piperidine (0.94 g), and sodium methoxide in methanol (25%, 1.8 g) were stirred for 5 hours. The mixture was diluted with water (10 mL) and concentrated hydrochloric acid (1.7 mL). The mixture was washed with dichloromethane (10 mL), and 50% sodium hydroxide was added. The mixture was extracted with dichloromethane, and the extract was dried (MgSO$_4$), filtered and concentrated to give the title compound (1.6 g, 70%).

PREPARATION 4

1-(3-Chloropropane-1-sulfonyl)-4-(4-fluorophenyl) piperazine

The following is the preparation of a compound of formula 6 wherein L is chloro, m is 3, Y is —SO$_2$, and Z is (4-fluorophenyl)-piperazine.

To a 0° C. solution of 1-(4-fluorophenyl)piperazine (6.4 g, 35 mmol) in dichloromethane (50 mL) was added 3-chloropropanesulfonyl chloride (6.5 g, 37 mmol). The mixture was stirred for 2 hours with warming to room temperature and was then washed with saturated aqueous sodium bicarbonate. The dichloromethane solution was dried (Na$_2$SO$_4$) and evaporated in vacuo. Recrystallization of the crystalline residue from methanol gave the title compound as a white solid (9.2 g, 80%); m.p. 80–81° C.

PREPARATION 5

4-(3-Chloropropane-1-sulfonyl)piperazine-1-carboxylic acid tert-butyl ester

The following is the preparation of a compound of formula 6a wherein R$^3$ and R$^4$ are each hydrogen, L is chloro, m is 3, Y is —SO$_2$, and P is BOC.

To a 0° C. solution of piperazine-1-carboxylic acid tert-butyl ester (4.7 g, 25 mmol) and triethylamine (7 mL, 50 mmol) in dichloromethane (50 mL) was added 3-chloropropanesulfonyl chloride (4.4 g, 25 mmol). The mixture was stirred for 2 hours with warming to room temperature and was then washed sequentially with dilute aqueous hydrochloric acid and saturated aqueous sodium bicarbonate. The dichloromethane solution was dried (Na$_2$SO$_4$) and evaporated in vacuo to give the title compound as a white solid (7.4 g, 91%); m.p. 112–114° C.

PREPARATION 6

1-(3-Chloropropane-1-sulfonyl)-4-methylpiperazine

The following is the preparation of a compound of formula 6b wherein R$^3$ and R$^4$ are each hydrogen, L is chloro, m is 3, Y is —SO$_2$, and Z is 4-methylpiperazine.

To a cooled solution of N-methylpiperazine (8.49 g), toluene (43 mL), and sodium hydroxide (25%, 43 mL) was added a solution of 3-chloro-propanesulfonyl chloride (15 g) in toluene (30 mL) over a period 30 minutes. The mixture was stirred for 1 hour in a cold bath and then for another hour at room temperature. The top organic layer was separated, washed with aqueous sodium chloride, dried (MgSO$_4$), filtered, and concentrated to give the title compound (17.9 g, 88%); m.p. 43.0–44.5° C.

PREPARATION 7

2,3-Dihydrobenzo[1,4]dioxine-5-carboxylic acid (pyridin-4-ylmethyl)amide

The following is the preparation of a compound of formula 9 wherein R$^3$ and R$^4$ are each independently hydrogen.

A. N,N'-Carbonyldiimidazole (1.62 g, 10 mmol) was added to a stirred solution of 2,3-dihydrobenzo[1,4]dioxine-5-carboxylic acid (1.64 g, 10 mmol) in tetrahydrofuran (25 mL) and the resulting solution was heated at 60° C. for 15 minutes. The solution was cooled to room temperature and -4-(aminomethyl)pyridine (1.08 g, 10 mmol) was added. The reaction mixture was heated at 60° C. for 2 hours, cooled, poured into water, and extracted 3 times with ethyl acetate. The combined ethyl acetate extract was dried (Na$_2$SO$_4$) and evaporated in vacuo to a crystalline residue which was triturated with water, filtered, and dried in vacuo to give 2,3-dihydrobenzo[1,4]dioxine-5-carboxylic acid (pyridin-4-ylmethyl)amide as a white solid (1.95 g, 72%); m.p. 120–121° C.

B. To a mixture of 2,3-dihydrobenzo[1,4]dioxine-5-carboxylic acid ethyl ester (1087 g), methanol (500 mL) and toluene (44 g) at 35° C. was added 25% sodium methoxide in methanol (1193 mL). After 30 minutes, 4-(aminomethyl) pyridine (530 mL) was added, and the reaction mixture was warmed to a temperature of 50° C., maintained at 50° C. for 7 hours, and cooled to room temperature overnight. The reaction was then warmed to 30° C. and water (4.35 L) was added slowly over 40 minutes. The mixture was again cooled and aged at 5° C. overnight and filtered. The crystals were washed with water, and dried to give the title compound (1255 g, 89%); m.p. 123–124.5° C.

PREPARATION 8

1-(2,3-Dihydrobenzo[1,4]dioxin-5-yl)-3-hydroxy-3-pyridin-4-ylpropan-1-one

The following is the preparation of a compound of formula 11 wherein R$^1$ and R$^2$ are each independently hydrogen.

To a −60° C. solution of diisopropylamine (3.22 mL, 23 mmol) in tetrahydrofuran (35 mL) was added n-butyllithium (1.6 M in hexane, 14.4 mL). To the resulting solution was added 1-(2,3-dihydrobenzo[1,4]dioxin-5-yl)ethanone (prepared by the method described in U.S. Pat. No. 5,763, 458) (3.56 g, 20 mmol) in tetrahydrofuran (3 mL). The mixture was stirred at −60° C. for 10 minutes followed by the addition of pyridine-4-carboxaldehyde (2.36 g, 22 mmol). After stirring for an additional 40 minutes, the reaction mixture was treated with aqueous ammonium chloride solution, diluted with cold water, basified, and extracted with ethyl acetate. The combined organic extracts were washed with water and brine, dried, and the concentrated in vacuo to afford the crude title compound as a syrup which solidified (4.4 g, 77%). The product was directly used in the next step.

PREPARATION 9

1-(2,3-Dihydrobenzo[1,4]dioxin-5-yl)-3-pyridin-4-ylpropenone

The following is the preparation of a compound of formula 12 wherein R$^1$ and R$^2$ are each independently hydrogen.

To a cold solution of concentrated sulfuric acid (10 mL) was added 1-(2,3-dihydrobenzo[1,4]dioxin-5-yl)-3-hydroxy-3-pyridin-4-ylpropan-1-one (2.0 g). The reaction mixture was stirred at a temperature of about 10–20° C. for 30 minutes, then allowed to cool in an ice bath and stirred for an additional 15–30 minutes. The resultant solid was filtered, washed several times with water, and dried. The residue was suspended in cold water, basified with ammonium hydroxide, and extracted with dichloromethane. The combined organic extracts were washed with water and brine, dried ($Na_2SO_4$) and solvent evaporated in vacuo to give the title compound as a syrup (3.9 g) which was directly used in the next step.

PREPARATION 10

1-(2,3-Dihydrobenzo[1,4]dioxin-5-yl)-3-pyridin-4-ylpropan-1-one

The following is the preparation of a compound of formula 13 wherein $R^1$ and $R^2$ are each independently hydrogen.

A solution of 1-(2,3-dihydrobenzo[1,4]dioxin-5-yl)-3-pyridin-4-ylpropenone (3.9 g, 14.59 mmol) in ethyl acetate (70 mL) was hydrogenated over 10% palladium on carbon (0.4 g) at atmospheric pressure for 5 hours. The catalyst was removed by filtration through Celite® and the filtrate concentrated in vacuo to give the title compound as a yellow solid (2.75 g, 51% overall yield); $^1$H NMR (CDCl$_3$) 8.48 (dd, 2H), 7.29 (dd, 1H), 7.17 (dd, 2H), 7.02 (dd, 1H), 6.87 (dd, 1H), 4.30 (m, 4H), 3.30 (t, 2H), 3.02 (t, 2H).

EXAMPLE 1

2,3-Dihydrobenzo[1,4]dioxine-5-carboxylic acid(1-{3-[4[(4-fluorophenyl)-piperazine-1-sulfonyl]-propyl}piperidin-4-ylmethyl)amide The following is the preparation of a compound of Formula I wherein $R^1$ and $R^2$ are each independently hydrogen, X is —NH, m is 3, Y is —SO$_2$, and Z is (4-fluorophenyl)-piperazine.

A mixture of 2,3-dihydrobenzo[1,4]dioxine-5-carboxylic acid (piperidin-4-ylmethyl)amide (426 mg, 1.54 mmol), 1-(3-chloropropane-1-sulfonyl)-4-(4-fluorophenyl) piperazine (495 mg, 1.54 mmol), sodium iodide (230 mg, 1.54 mmol), and triethylamine (200 mg, 2 mmol) in N,N-dimethylformamide (5 mL) was stirred at 85° C. for 12 hours. The cooled reaction mixture was partitioned between ethyl acetate and saturated aqueous sodium bicarbonate. The ethyl acetate layer was washed with water (three times) and brine, and the organic layer dried ($Na_2SO_4$) and evaporated in vacuo. The crude product was purified by silica gel chromatography (5% methanol-dichloromethane) to give the title compound (350 mg, 40%). The dihydrochloride salt of the title compound was crystallized from ethanol; m.p. 220° C. Analysis for $C_{28}H_{37}N_4O_5S$ 2 HCl: Calcd.: C, 53.08; H, 6.20; N, 8.84. Found: C, 52.87; H, 6.15; N, 8.86.

Proceeding as in Example 1, but replacing 1-(3-chloropropane-1-sulfonyl)-4-(4-fluorophenyl)piperazine with other alkyl halides, and then correspondingly as in Example 1, the following compounds of Formula I were prepared:

2,3-dihydrobenzo[1,4]dioxine-5-carboxylic acid{1-[3-(morpholine-4-sulfonyl)propyl]piperidin-4-ylmethyl}amide, hydrochloride salt; m.p. 192–195° C.;

2,3-dihydrobenzo[1,4]dioxine-5-carboxylic acid{1-[3-(4-methylpiperazine-1-sulfonyl)propyl]piperidin-4-ylmethyl}amide; m.p. 160–163° C.;

2,3-dihydrobenzo[1,4]dioxine-5-carboxylic acid{1-[3-(4-methylpiperazine-1-sulfonyl)propyl]piperidin-4-ylmethyl}amide, dihydrochloride salt; m.p. 186–189° C.;

2,3-dihydrobenzo[1,4]dioxine-5-carboxylic acid{1-[3-(4-ethylpiperazine-1-sulfonyl)propyl]piperidin-4-ylmethyl}amide; dihydrochloride salt: m.p. 220–224° C.;

2,3-dihydrobenzo[1,4]dioxine-5-carboxylic acid{1-[3-(4-propylpiperazine-1-sulfonyl)propyl]piperidin-4-ylmethyl}amide, dihydrochloride salt; m.p. 243–245° C.;

2,3-dihydrobenzo[1,4]dioxine-5-carboxylic acid{1-[3-(4-isopropyl-piperazine-1-sulfonyl)propyl]piperidin-4-ylmethyl}amide, dihydrochloride salt; m.p. 233–236° C.;

2,3-dihydrobenzo[1,4]dioxine-5-carboxylic acid{1-[3-(4-isobutylpiperazine-1-sulfonyl)propyl]piperidin-4-ylmethyl}amide, dihydrochloride salt; m.p. 270–271° C.;

2,3-dihydrobenzo[1,4]dioxine-5-carboxylic acid{1-[3-(4-cyclopentyl-piperazine-1-sulfonyl)propyl]piperidin-4-ylmethyl}amide, dihydrochloride salt; m.p. 245–246° C.;

2,3-dihydrobenzo[1,4]dioxine-5-carboxylic acid{1-[3-(4-pyrimidin-2-ylpiperazine-1-sulfonyl)propyl]piperidin-4-ylmethyl}amide; m.p. 173–177° C.;

2,3-dihydrobenzo[1,4]dioxine-5-carboxylic acid{1-[3-(4-acetylpiperazine-1-sulfonyl)propyl]piperidin-4-ylmethyl}amide, hydrochloride salt; m.p. 204–208° C.;

2,3-dihydrobenzo[1,4]dioxine-5-carboxylic acid(1-{3-[4-(furan-2-carbonyl)-piperazine-1-sulfonyl]propyl}piperidin-4-ylmethyl)amide, hydrochloride salt; m.p.148–150° C.;

2,3-dihydrobenzo[1,4]dioxine-5-carboxylic acid(1-{3-[4-(tetrahdropyran-4-carbonyl)piperazine-1-sulfonyl]propyl}piperidin-4-ylmethyl)amide, hydrochloride salt; m.p. 250–251° C.;

2,3-dihydrobenzo[1,4]dioxine-5-carboxylic acid(1-{3-[4-(pyridine-3-carbonyl)piperazine-1-sulfonyl]propyl}piperidin-4-ylmethyl)amide, dihydrochloride salt; m.p. indefinite;

2,3-dihydrobenzo[1,4]dioxine-5-carboxylic acid{1-[3-(4-methanesulfonyl-piperazine-1-sulfonyl)propyl]piperidin-4-ylmethyl)amide, hydrochloride salt; m.p. 236° C.;

2,3-dihydrobenzo[1,4]dioxine-5-carboxylic acid(1-{3-[4-(isopropane-2-sulfonyl)piperazine-1-sulfonyl]propyl}piperidin-4-ylmethyl)amide, hydrochloride salt; m.p. 165–170° C.;

2,3-dihydrobenzo[1,4]dioxine-5-carboxylic acid(1-{3-[4-(4-fluorobenzene-sulfonyl)piperazine-1-sulfonyl]propyl}piperidin-4-ylmethyl)amide, hydrochloride salt; m.p. 185–186° C.;

2,3-dihydrobenzo[1,4]dioxine-5-carboxylic acid(1-{3-[4-(pyrrolidine-1-sulfonyl)piperazine-1-sulfonyl]propyl}piperidin-4-ylmethyl)amide, hydrochloride salt; m.p. 181–182° C.;

2,3-dihydrobenzo[1,4]dioxine-5-carboxylic acid(1-[3-(piperidine-1-sulfonyl)propyl]piperidin-4-ylmethyl}amide, hydrochloride salt; m.p. 165–168° C.;

2,3-dihydrobenzo[1,4]dioxine-5-carboxylic acid{1-[3-(4,4-dimethyl-piperidine-1-sulfonyl)propyl]piperidin-4-ylmethyl}amide, hydrochloride salt; m.p. 108° C.;

2,3-dihydrobenzo[1,4]dioxine-5-carboxylic acid{1-[3-(8-azaspiro[4.5]-decane-8-sulfonyl)propyl]piperidin-4-ylmethyl}amide, hydrochloride salt; m.p. 160–165° C.;

2,3-dihydrobenzo[1,4]dioxine-5-carboxylic acid{1-[3-(4-propylpiperidine-1-sulfonyl)propyl]piperidin-4-ylmethyl}amide, hydrochloride salt; m.p. 125° C.;

2,3-dihydrobenzo[1,4]dioxine-5-carboxylic acid{1-[3-(4-methoxypiperidine-1-sulfonyl)propyl]piperidin-4-ylmethyl}amide, hydrochloride salt; m.p. indefinite;

2,3-dihydrobenzo[1,4]dioxine-5-carboxylic acid{1-[3-(4-carboxamido-piperidine-1-sulfonyl)propyl]piperidin-4-ylmethyl}amide, hydrochloride salt; m.p.177–180° C.;

2,3-dihydrobenzo[1,4]dioxine-5-carboxylic acid(1-{3-[4-(methanesulfonyl-amino-methyl)piperidine-1-sulfonyl]propyl}piperidin-4-ylmethyl)amide, hydrochloride salt; m.p. 121–123° C.; and 2,3-dihydrobenzo[1,4]dioxine-5-carboxylic acid(1-{3-[methyl-(1-methylpiperidin-4-yl)sulfamoyl]propyl}piperidin-4-ylmethyl)amide, hydrochloride salt; m.p. 218–219° C.

EXAMPLE 2

2,3-Dihydrobenzo[1,4]dioxine-5-carboxylic acid{1-[3-(piperazine-1-sulfonyl)-propyl]piperidin-4-ylmethyl}amide The following is the preparation of a compound of Formula Ia wherein $R^1$, $R^2$, $R^3$, and $R^4$ are each independently hydrogen, m is 3, and Y is —$SO_2$.

A mixture of 2,3-dihydrobenzo[1,4]dioxine-5-carboxylic acid(piperidin-4-ylmethyl)amide (28.6 g, 104 mmol), 4-(3-chloropropane-1-sulfonyl)piperazine-1-carboxylic acid tert-butyl ester (33.9 g, 104 mmol), sodium iodide (7.8 g, 52 mmol), and triethylamine (29 mL, 209 mmol) in N,N-dimethylformamide (70 mL) was stirred at 90° C. for 4 hours. The cooled reaction mixture was partitioned between ethyl acetate and water. The ethyl acetate layer was washed with water (three times) and brine, dried ($Na_2SO_4$) and the solvents evaporated in vacuo. The crude product was purified by silica gel chromatography (5% methanol-dichloromethane) and crystallization from ethyl acetate-hexane to give 4-[3-(4-{[2,3-dihydrobenzo[1,4]dioxin-5-carbonyl)amino]-methyl}piperidin-1-yl)propane-1-sulfonyl]piperazine-1-carboxylic acid tert-butyl ester (37.5 g, 64%); m.p. 130–132° C. Analysis for $C_{27}H_{43}N_4O_7$ S: Calcd.: C, 57.12; H, 7.63; N, 9.87. Found: C, 57.01; H, 7.40; N, 9.94.

A solution of 4-[3-(4-{[2,3-dihydrobenzo[1,4]dioxin-5-carbonyl)amino]-methyl}piperidin-1-yl)propane-1-sulfonyl]piperazine-1-carboxylic acid tert-butyl ester (5.7 g, 10 mmol) in dichloromethane (20 mL) was treated with trifluoroacetic acid (8 mL) and the resulting solution was stirred at room temperature for 1 hour. Copious amounts of gas were evolved. The mixture was concentrated in vacuo and the residue was partitioned between dichloromethane and brine, and the aqueous layer was made basic by addition of aqueous ammonium hydroxide solution. The layers were separated and the aqueous layer was extracted with dichloromethane. The combined dichloromethane extract was dried ($Na_2SO_4$) and evaporated in vacuo. The residue was dissolved in ethanol (50 mL) and the solution was made acidic with ethanolic hydrochloric acid. Crystallization was induced by addition of a small amount of ether. Filtration gave the dihydrochloride salt of the title compound (5.1 g, 93%); m.p. 92–94° C.

EXAMPLE 3

2,3-Dihydrobenzo[1,4]dioxine-5-carboxylic acid{1-3-(piperazine-1-sulfonyl)-propyl]piperidin-4-ylmethyl}amide The following is an alternative preparation of a compound of Formula Ia wherein $R^1$, $R^2$, $R^3$, and $R^4$ are each independently hydrogen, m is 3, and Y is —$SO_2$.

A stirred solution of the 2,3-dihydrobenzo[1,4]dioxine-5-carboxylic acid (pyridin-4-ylmethyl)amide (1.30 g, 4.8 mmol) and 4-(3-iodopropane-1-sulfonyl)piperazine-1-carboxylic acid tert-butyl ester (prepared from the corresponding chloro compound by treatment with sodium iodide in actone) (2.12 g, 5.1 mmol) in acetonitrile (25 mL) was heated under reflux for 8 hours. The mixture was concentrated in vacuo and the residue was triturated with ethyl acetate. Filtration gave the crude pyridinium iodide which was dissolved in methanol (25 mL) and water (5 mL), and hydrogenated over platinum(IV) oxide (450 mg) at atmospheric pressure for 16 hours. The mixture was filtered through Celite® and the filtrate was partitioned between dichloromethane and aqueous ammonium hydroxide. The dichloromethane was dried ($Na_2SO_4$) and evaporated in vacuo. Purification of the residue by silica gel chromatography gave 4-[3-(4-{[2,3-dihydrobenzo[1,4]dioxin-5-carbonyl)amino]methyl}pyridin-1-yl)propane-1-sulfonyl]piperazine-1-carboxylic acid tert-butyl ester (1.05 g, 39%).

The 4-[3-(4-{[2,3-dihydrobenzo[1,4]dioxin-5-carbonyl)amino]methyl}pyridin-1-yl)propane-1-sulfonyl]piperazine-1-carboxylic acid tert-butyl ester was treated with trifluoroacetic acid as described in Example 2 to give the title compound which was identical to the material prepared in Example 2.

EXAMPLE 4

2,3-Dihydrobenzo[1,4]dioxine-5-carboxylic acid(1-{3-[4-(propane-1-sulfonyl)piperazine-1-sulfonyl]propyl}piperidin-4-ylmethyl)amide The following is the preparation of a compound of Formula Ib wherein $R^1$, $R^2$, $R^3$, and $R^4$ are each independently hydrogen, $R^6$ is propane-1-sulfonyl, m is 3, and Y is —$SO_2$.

To a 0° C. solution of the 2,3-dihydrobenzo[1,4]dioxine-5-carboxylic acid{1-[3-(piperazine-1-sulfonyl)-propyl]piperidin-4-ylmethyl}amide dihydrochloride (378 g, 0.7 mmol) and triethylamine (233 mg, 2.3 mmol) in dichloromethane (10 mL) was added 1-propanesulfonyl chloride (110 mg, 0.8 mmol). The mixture was stirred for 2 hours with warming to room temperature, diluted with dichloromethane, and washed with saturated aqueous sodium bicarbonate and brine. The dichloromethane extract was dried ($Na_2SO_4$) and evaporated in vacua. Purification by silica gel chromatography (7% methanol-dichloromethane) gave the title compound (the free base) as a white solid (167 mg, 42%). The hydrochloride salt was crystallized from ethanolic-hydrochloric acid by addition of ether; m.p. 201–202° C. Analysis for $C_{25}H_{40}N_4O_7S_2$ HCl. 0.3 $H_2O$: Calcd.: C, 48.86; H, 6.82; N, 9.12. Found: C, 48.87; H, 6.67; N, 9.04.

EXAMPLE 5

2,3-Dihydrobenzo[1,4]dioxine-5-carboxylic acid{1-[3-(4-methylpiperazine-1-sulfonyl)propyl]piperidin-4-ylmethyl}amide The following is an alternative preparation of a compound of Formula Ib wherein $R^1$, $R^2$, $R^3$, and $R^4$ are each independently hydrogen, $R^6$ is methyl, m is 3, and Y is —$SO_2$.

A mixture of the 2,3-dihydrobenzo[1,4]dioxine-5-carboxylic acid{1-[3-piperazine-1-sulfonyl)-propyl]piperidin-4-ylmethyl}amide dihydrochloride (25 g, 46 mmol) and 10% palladium on carbon (2.2 g) in 50% ethanol-water (200 mL) and 37% aqueous formaldehyde solution (25 mL) was acidified by addition of several drops of hydrochloric acid and then stirred under an atmosphere of hydrogen at room temperature for 12 hours. The catalyst was removed by filtration through Celite® and the filtrate was concentrated in vacuo. The residue was partitioned between aqueous ammonium hydroxide and dichloromethane, and the dichloromethane was dried ($Na_2SO_4$), evaporated, and crystallized from ethanol to give the title compound (free base) as a white crystalline solid (20.8 g); m.p. 163.5–164.5° C. Analysis for $C_{23}H_{36}N_4O_5S$: Calcd.: C, 57.48; H, 7.55; N, 11.66. Found: C, 57.59; H, 7.58; N, 11.66.

The free base was dissolved in ethanol and ethanolic-hydrochloric acid was added until the solution was strongly acidic (pH paper). The resultant precipitate was filtered and washed with ether to give the dichloride salt of the title compound (22.2 g, 87%); m.p. 186–189° C. Analysis for $C_{23}H_{36}N_4O_5S \cdot 2HCl \cdot 0.25 H_2O$: Calcd.: C, 49.50; H, 6.95; N, 10.04. Found: C, 49.41; H, 6.93; N, 10.03.

Proceeding as described above in Example 5, but replacing 2,3-dihydrobenzo-[1,4]dioxine-5-carboxylic acid{1-[3-piperazine-1-sulfonyl)-propyl]piperidin-4-ylmethyl}amide dihydrochloride with 7-chloro-2,3-dihydrobenzo[1,4]dioxine-5-carboxylic acid{1-[3-(piperazine-1-sulfonyl)propyl]piperidin-4-ylmethyl}amide; and utilizing 10% palladium on carbon with Raney nickel as the hydrogenation catalyst, the following compound of Formula I was prepared:

7-chloro-2,3-dihydrobenzo[1,4]dioxine-5-carboxylic acid{1-[3-(4-methylpiperazine-1-sulfonyl)propyl]piperidin-4-ylmethyl}amide, dichloride salt; m.p. 223–225° C. Analysis for $C_{23}H_{35}ClN_4O_5S \cdot 2 HCl \cdot 0.35 H_2O$: Calcd.: C, 46.48; H, 6.39; N, 9.43. Found: C, 46.48; H, 6.29; N, 9.39.

EXAMPLE 6

2,3-Dihydrobenzo[1,4]dioxine-5-carboxylic acid{1-[3-(4-methylpiperazine-1-sulfonyl)propyl]piperidin-4-ylmethyl}amide The following is the alternative preparation of a compound of Formula Ib wherein $R^1$, $R^2$, $R^3$, and $R^4$ are each independently hydrogen, $R^6$ is methyl, m is 3, and Y is —$SO_2$.

A mixture of 2,3-dihydrobenzo[1,4]dioxine-5-carboxylic acid(piperidin-4-ylmethyl)amide hydrochloride (2.0 g), potassium bromide (0.95 g), tetra-n-butylammonium bromide (0.165 g), trisodium phosphate dodecahydrate (6.03 g), water (6 mL), 1-(3-chloropropane-1-sulfonyl)-4-methylpiperazine (1.69 g), and toluene (28 mL) was refluxed for 21 hours. While still warm the top organic layer was separated, diluted with toluene (13.6 mL), partially concentrated by distillation, and cooled. The crystals were filtered, washed with toluene, and dried to give the title compound (2.82 g, 92%); m.p. 161–162° C.

EXAMPLE 7

1-(2,3-Dihdrobenzo[1,4]dioxin-5-yl)-3-{1-[3-(morpholine-4-sulfonyl)propyl]piperidin-4-yl}propan-1-one The following is the preparation of a compound of Formula Ic wherein $R^1$ and $R^2$ are each independently hydrogen, m is 3, Y is —$SO_2$, and Z is morpholino.

A mixture of 1-(2,3-dihdrobenzo[1,4]dioxin-5-yl)-3-pyridin-4-yl-propan-1-one (500 mg, 1.86 mmol), 4-(3-chloropropane-1-sulfonyl)morpholine (500 mg, 2.23 mmol) and potassium iodide (20 mg) in acetonitrile (12 mL) was heated under reflux for 16 hours. The reaction mixture was concentrated in vacuo. The residual crude pyridinium salt was dissolved in N,N-dimethylformamide (10 mL) and hydrogenated over platinum (IV) oxide (100 mg) at atmospheric pressure for 3 hours. The mixture was filtered and the filtrate was concentrated in vacuo. The residue was partitioned between dichloromethane and aqueous ammonium hydroxide and the organic layer was dried ($Na_2SO_4$) and evaporated in vacuo. Purification by silica gel chromatography and followed by treatment with ethanolic-hydrochloric acid and ether gave the hydrochloride salt of the title compound (560 mg, 60%); m.p. 173–175° C. Analysis for $C_{23}H_{35}N_2O_6S \cdot HCl$: Calcd.: C, 55.92; H, 7.01; N, 5.57. Found: C, 55.14; H, 7.05; N, 5.72.

EXAMPLE 8

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing 100 mg each; one capsule would approximate a total daily dosage.

EXAMPLE 9

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

EXAMPLE 10

Composition for Oral Administration

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |

-continued

| Ingredient | Amount |
| --- | --- |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

EXAMPLE 11

Parenteral Formulation (IV)

| Ingredient | % wt./wt. |
| --- | --- |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

EXAMPLE 12

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 13

Topical Formulation

| Ingredients | grams |
| --- | --- |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

EXAMPLE 14

Nasal Spray Formulations

Several aqueous suspensions containing from 0.025–0.5 percent active compound are prepared as nasal spray formulations. The formulations optionally contain inactive ingredients such as microcrystalline cellulose, sodium carboxymethylcellulose, dextrose, and the like. Hydrochloric acid may be added to adjust pH. The nasal spray formulations may be delivered via a nasal spray metered pump typically delivering 50–100 microliters of formulation per actuation. A typical dosing schedule is 2–4 sprays every 4–12 hours.

EXAMPLE 15

Thoracic Esophagus 5-$HT_4$ Receptor Assay

The following describes an in vitro assay which utilizes rat isolated esophageal muscularis mucosae to identify test compounds which are 5-$HT_4$ receptor antagonists.

Thoracic esophagi are isolated from male Sprague-Dawley rats and placed in Tyrode's solution. The outer striated muscle is removed to reveal the muscularis mucosae ("mm"). Each mm is suspended vertically in a 10 mL tissue bath containing methylsergide (1 $\mu$M), cocaine (30 $\mu$M), and corticosterone (30 $\mu$M) in Tyrode's solution maintained at 37° C., and constantly aerated with a 95% oxygen and 5% carbon dioxide gas mixture.

A resting tension of 1 g is applied to each tissue and thereafter 0.5 g tension is reapplied at 15 minute intervals. A steady state contraction to carbachol (3 $\mu$M) is produced, and then the tissue is exposed to 5-HT in a cumulative-concentration fashion, increasing in concentration until maximal or near maximal relaxation is achieved. The 5-HT produces a concentration-dependent 5-$HT_4$ mediated relaxation of the mm.

The tissue is exposed to agonist-free Tyrode's solution for 30 minutes and then again contracted with carbachol. The tissue is then exposed to the test compound. If the test compound does not itself elicit relaxation of the mm, the tissue is exposed to 5-HT in the presence of the test compound. Compounds which inhibit the relaxation responses to 5-HT are characterized as 5-$HT_4$ receptor antagonists.

Proceeding as in Example 15, the compounds of the invention were evaluated and found to be 5-$HT_4$ receptor antagonists.

EXAMPLE 16

Pig Tachycardia Assay

The following describes an in vivo assay for determining the inhibitory effects of compounds of this invention on 5-HT-induced heart rate increases in anesthetized and vagotomized Yucatan micropigs.

The animals were surgically prepared prior to conducting the experiments. Briefly, Yucatan micropigs were chemically restrained, anesthetized, intubated with a cuffed endotracheal tube, and ventilated with room air under positive pressure. Needle electrodes were placed subcutaneously to record a limb lead II electrocardiogram, and the right femoral artery and vein were isolated by blunt dissection. In the intravenous study, two polyethylene cannulae were inserted into the femoral vein, the first for infusion of sodium pentobarbital to maintain a stable plane of anesthesia, and the second for administration of 5-HT and test compound. In the intraduodenal study, a partial midline laparatomy was performed and a polyethylene cannula was inserted into the duodenum for administration of the test compound. The aortic blood pressure and heart rate were measured, and periodic withdrawals of blood samples were performed for blood gas analyses and for determination of plasma compound level. Following a cervical midline incision, both vagus nerves were exposed and severed to abolish vagally-mediated parasympathetic influences on the heart rate. The body temperature was monitored and body heat was maintained. Heparinized saline (50 units heparin sodium per ml) was used to maintain the patency of each vascular cannula throughout the experiment.

Following the surgical preparation, each animal was allowed to equilibrate and stabilize for at least 20 minutes before beginning an experiment. Ascending doses of 5-HT at full-log intervals (0.3–300 µg/kg, iv) were administered at 5 to 15 minute intervals to each animal (followed by a 2 mL saline flush) to construct a 5-HT dose-response curve in which responses were expressed as change in heart rate from baseline. A dose that induced a 50% of maximal increase in heart rate ($ED_{50}$) was graphically selected and repeated in triplicate at 5 to 10 minute intervals to determine a control (pre-dose) response.

In an intravenous dose-response study following the final control period, multiple intravenous doses of the test compound were administered cumulatively at half-log intervals with approximately 30 minute intervals between each dose. A 2 mL saline flush was given after each dose. Each animal was subsequently challenged intravenously with its respective 5-HT $ED_{50}$ dose at 5 and 15 minutes after each dose of the test compound.

In an intraduodenal dose-response study following the final control period, multiple intraduodenal doses of the test compound were administered cumulatively at half-log intervals with a 60 minute interval between each dose. A 3 mL saline flush was given after each dose. Each animal was subsequently challenged intravenously with its respective 5-HT $ED_{50}$ dose at 15, 30, and 45 minutes after each dose of the test compound.

In an intraduodenal duration study following the final control period, a single dose of the test compound which generally produced approximately 70% inhibition of 5-HT-induced heart rate increases in the intraduodenal dose-response study, or vehicle (deionized water, 0.5 mvkg) was administered. A 3 mL saline flush was given after each dose. Each animal was subsequently challenged intravenously with its respective 5-HT $ED_{50}$ dose at 15, 30, 45, and 60 minute post dose and at 30 minute intervals thereafter for the duration of the 6 hour experiment.

Proceeding as in Example 16, a number of compounds of the invention were evaluated and found to be inhibitors of 5-HT induced tachycardia.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound comprising Formula I:

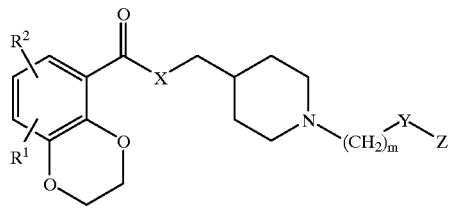

I wherein:
$R^1$ and $R^2$ are each independently in each occurrence hydrogen, lower alkyl, alkoxy, halogen, amino or hydroxy;
X is independently in each occurrence —NH or —$CH_2$;
m is independently in each occurrence an integer 2, 3, or 4;
Y is independently in each occurrence —$SO_2$;
Z is independently in each occurrence formula (A) or (B):

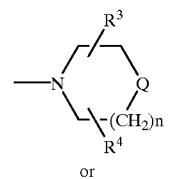

(A)

or

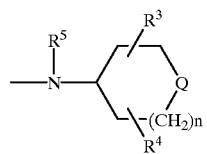

(B)

wherein:
$R^3$, $R^4$, and $R^5$ are each independently in each occurrence hydrogen or lower alkyl;
Q is independently in each occurrence O, S, —$NR^6$, or —$CR^7R^8$;
n is independently in each occurrence an integer 1 or 2;
wherein:
$R^6$ is independently in each occurrence hydrogen, lower alkyl, cycloalkyl, heterocyclyl, heteroaryl, —$COR^9$, —$SO_2R^9$, —$CONR^{10}R^{11}$, —$SO_2NR^{10}R^{11}$, or aryl optionally mono- or di-substituted with halogen or lower alkyl;
$R^7$ is independently in each occurrence hydrogen or lower alkyl;
$R^8$ is independently in each occurrence hydrogen, lower alkyl, alkoxy, aryloxy, —$(CH_2)_pCONR^{10}R^{11}$, —$(CH_2)_pSO_2NR^{10}R^{11}$, —$(CH_2)_pNR^7COR^9$, or —$(CH_2)_pNR^7SO_2R^9$; or
$R^7$ and $R^8$ taken together with the common ring carbon to which they are attached form a monocyclic saturated 5- or 6-membered ring optionally independently containing 0 or 1 heteroatom of nitrogen, oxygen, or sulfur;
wherein:
p is independently in each occurrence an integer 0, 1, 2, 3 or 4;

R⁹ is independently in each occurrence lower alkyl, heteroaryl, heterocyclyl, or aryl optionally mono- or di-substituted with halogen or lower alkyl; and R¹⁰ and R¹¹ are each independently hydrogen or lower alkyl;

or an individual isomer, a racemic or non-racemic mixture of isomers, or a pharmaceutically acceptable salt or hydrate thereof.

2. The compound of claim 1 wherein $R^1$ and $R^2$ are each independently hydrogen.

3. The compound of claim 2 wherein Y is —SO$_2$ and m is 3.

4. The compound of claim 3 wherein X is —NH.

5. The compound of claim 4 wherein Z is formula (A), n is 1, and $R^3$ and $R^4$ are each independently hydrogen.

6. The compound of claim 5 wherein Q is —NR⁶.

7. The compound of claim 6 wherein $R^6$ is lower alkyl or cycloalkyl.

8. The compound of claim 7 wherein $R^6$ is methyl, ethyl, propyl, isopropyl, butyl, isobutyl, or cyclopentyl.

9. The compound of claim 8 wherein $R^6$ is methyl.

10. The compound of claim 6 wherein $R^6$ is aryl optionally mono- or di-substituted with halogen, or —SO$_2$R⁹.

11. The compound of claim 10 wherein $R^6$ is independently phenyl, 4-fluorophenyl, or 4-chlorophenyl.

12. The compound of claim 10 wherein $R^9$ is independently lower alkyl or aryl optionally mono- or di-substituted with halogen or lower alkyl.

13. The compound of claim 12 wherein $R^9$ is independently methyl, ethyl, propyl, isopropyl, butyl, isobutyl, phenyl, 4-fluorophenyl, or 4-chlorophenyl.

14. The compound of claim 5 wherein Q is —CR⁷R⁸.

15. The compound of claim 14 wherein $R^7$ and $R^8$ are each independently hydrogen or lower alkyl.

16. The compound of claim 15 wherein $R^7$ and $R^8$ are each independently hydrogen, methy, ethyl, or propyl.

17. The compound of claim 14 wherein $R^7$ and $R^8$ taken together with the common ring carbon to which they are attached form a monocyclic saturated 5- or 6-membered ring optionally independently containing 0, or 1 heteroatom of nitrogen, oxygen, or sulfur.

18. The compound of claim 17 wherein $R^7$ and $R^8$ taken together with the common ring carbon to which they are attached form a monocyclic saturated 5-membered ring containing 0 heteroatoms.

19. The compound of claim 3 wherein X is —CH$_2$.

20. The compound of claim 19 wherein Z is formula (A), n is 1, and $R^3$ and $R^4$ are each independently hydrogen.

21. The compound of claim 20 wherein Q is O.

22. The compound of claim 1, or an individual isomer, a racemic or non-racemic mixture of isomers, or a pharmaceutically acceptable salt or solvate thereof comprising:

(a)

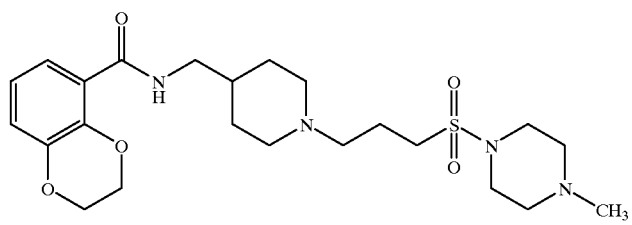

(b)

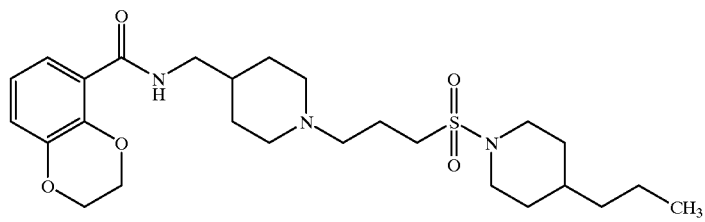

(c)

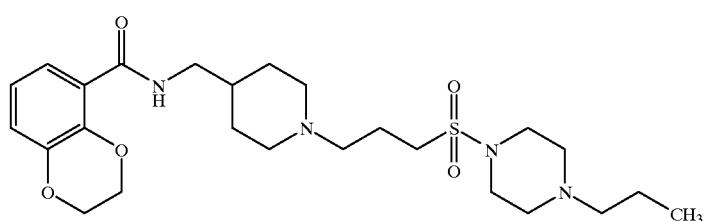

-continued
(d)
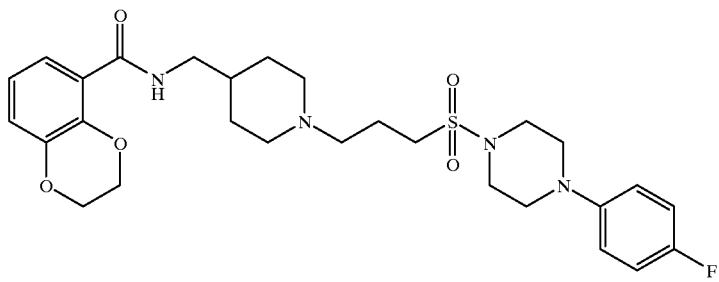
(e)
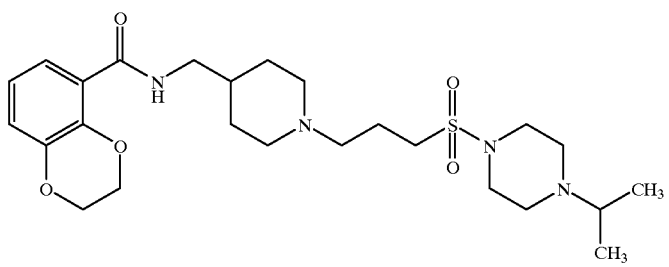
(f)
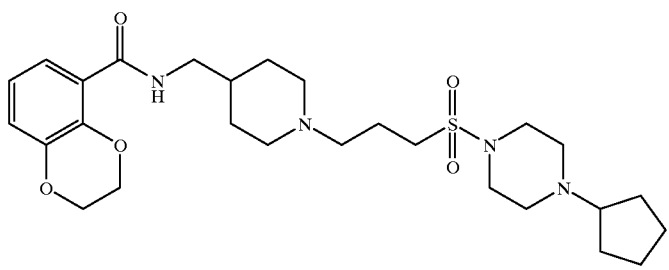
(g)
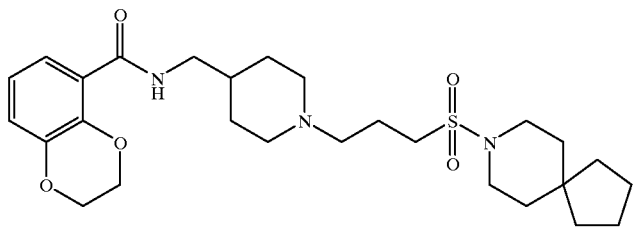
(h)
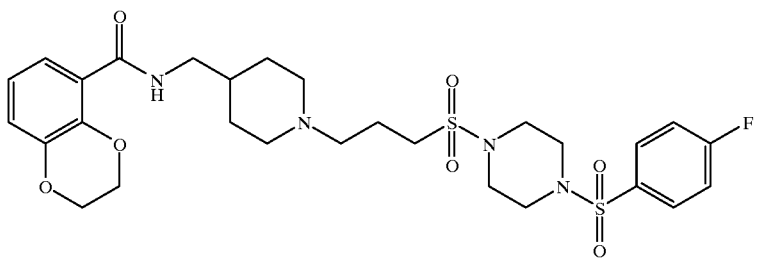
(i)
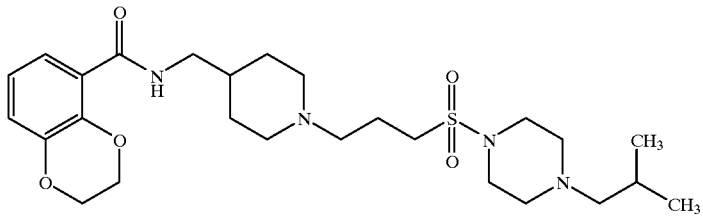

-continued

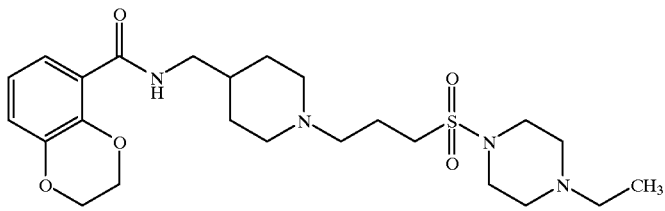
(j)

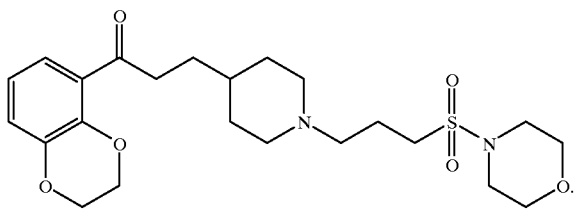
(k)

23. A pharmaceutical composition comprising a therapeutically effective amount of at least one compound of claim 1 or 22 in admixture with at least one suitable carrier.

24. The pharmaceutical composition of claim 23 wherein the at least one compound is suitable for administration to a subject having a disease state which is alleviated by treatment with a 5-HT$_4$ modulator.

25. A pharmaceutical composition suitable for administration to a subject comprising a therapeutically effective amount of at least one compound of claim 1 or 22 in admixture with at least one pharmaceutically acceptable carrier.

26. A method of treatment comprising administering to such a subject in need of such treatment, a therapeutically effective amount of at least one compound of claim 1 or 22.

27. The method of claim 26 wherein the subject suffers from a urinary tract disease state.

28. The method of claim 27 wherein the urinary disease state is overactive bladder, outlet obstruction, outlet insufficiency, or pelvic hypersensitivity.

29. The method of claim 28 wherein the urinary tract disorder is urgency, frequency, altered bladder capacity, incontinence, micturition threshold, unstable bladder contractions, sphincteric spasticity, detrusor hyperreflexia (neurogenic bladder), detrusor instability, benign prostatic hyperplasia, urethral stricture disease, tumors, low flow rates, difficulty in initiating urination, urgency, suprapubic pain, urethral hypermobility, intrinsic sphincteric deficiency, mixed incontinence, stress incontinence, pelvic pain, interstitial (cell) cystitis, prostadynia, prostatis, vulvadynia, urethritis, orchidalgia.

30. The method of claim 26 wherein the subject suffers from a CNS disease state.

31. The method of claim 30 wherein the CNS disease state is migraine headache, anxiety, depression, cerebrovascular deficiency, psychoses, obsessive/compulsive disorder, convulsive disorder, cognitive disorder, anxiety/depression disorder, or improper thermoregulation.

32. The method of claim 30 wherein the CNS disease state is paranoia, schizophrenia, attention deficiency, autism; anorexia, bulimia; epilepsy, withdrawal from addictive substances; Parkinson's disease, dementia; anticipatory anxiety, depression, mania, seasonal affective disorder, convulsions associated with withdrawal from addictive substances, or anxiety associated with withdrawal from addictive substances.

33. The method of claim 26 wherein subject suffers from a gastrointestinal disease state.

34. The method of claim 33 wherein the gastrointestinal disease state is dyspepsia, gastric stasis, peptic ulcer, reflux esophagitis, bile reflux gastritis, pseudo-obstruction syndrome, diverticulitis, irritable bowel syndrome, inflammatory bowel disease, Crohn's disease, flatulence, biliary dysmotility, gastroparesis, retarded gastric emptying, acute and chronic diarrhea, diarrhea induced by cholera or carcinoid syndrome, disturbed colonic motility, or short-term prokinesis.

35. The method of claim 26 wherein the subject suffers from a carciovascular disease state.

36. The method of claim 35 wherein the cardiovascular disease state is bradyarrhythmia, supraventricular arrhythmia, atrial fibrillation, atrial flutter, or atrial tachycardia.

37. The method of claim 26 wherein the compound is a 5-HT$_4$ receptor modulator.

38. The method of claim 37 wherein the compound is a 5-HT$_4$ receptor antagonist.

* * * * *